(12) United States Patent
Fotouhi et al.

(10) Patent No.: US 6,281,356 B1
(45) Date of Patent: Aug. 28, 2001

(54) SUBSTITUTED PYRROLES

(75) Inventors: Nader Fotouhi, Chatham; Norman Kong, West Caldwell; Allen John Lovey, North Caldwell, all of NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/737,685

(22) Filed: Dec. 15, 2000

Related U.S. Application Data

(60) Provisional application No. 60/171,557, filed on Dec. 22, 1999.

(51) Int. Cl.⁷ .................. C07D 401/14; C07D 403/14; C07D 413/14
(52) U.S. Cl. .............. 544/143; 548/455; 548/312.1; 548/181; 548/364.7; 548/214; 546/201; 544/333; 544/373
(58) Field of Search .................. 548/455, 312.1, 548/181, 364.7, 214; 544/333, 373, 143; 546/201

(56) References Cited

U.S. PATENT DOCUMENTS

| | | |
|---|---|---|
| 5,057,614 | 10/1991 | Davis et al. . |
| 5,380,746 | 1/1995 | Barth et al. . |
| 5,856,517 | 1/1999 | Huryn et al. . |
| 5,891,901 | 4/1999 | Dhingra et al. . |

FOREIGN PATENT DOCUMENTS

| | | |
|---|---|---|
| WO 93/18765 | 9/1993 | (WO) . |
| WO 98/04551 | 2/1998 | (WO) . |

*Primary Examiner*—Joseph K. McKane
*Assistant Examiner*—Andrea M. D'Souza
(74) *Attorney, Agent, or Firm*—George W. Johnston; Patricia S. Rocha-Tramaloni; Robert A. Silverman

(57) ABSTRACT

Disclosed are substituted pyrroles having the formula

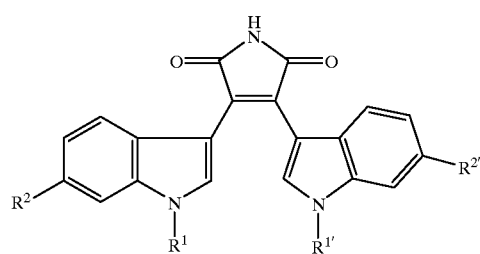

These compounds and their pharmaceutically acceptable salts are useful in the treatment and/or control of cell proliferative disorders, in particular cancer. Also disclosed are pharmaceutical compositions containing the foregoing compounds.

87 Claims, No Drawings

SUBSTITUTED PYRROLES

This application claims priority under 35 U.S.C. §119(e) of provisional application Ser. No. 60/171,557, filed Dec. 22, 1999.

BRIEF SUMMARY OF THE INVENTION

The invention relates to substituted pyrroles. More particularly, the invention relates to substituted pyrroles of the formula

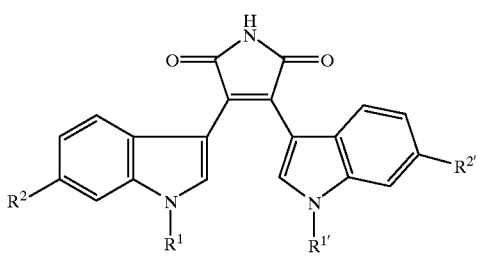

wherein
- $R^1$ and $R^{1'}$ are independently hydrogen, lower alkyl, lower alkenyl or lower alkynyl;
- $R^2$ is hydrogen, nitro, cyano, halogen, lower alkyl, lower alkenyl, lower alkynyl, or lower alkoxy; and
- $R^{2'}$ is a heteroaryl, heterocycle, ethyl substituted with a heteroaryl, or ethoxy substituted with a heteroaryl or heterocycle; or a pharmaceutically acceptable salt thereof.

The compounds of the invention are useful in the treatment or control of cell proliferative disorders, in particular cancer, particularly the treatment or control of solid tumors. In particular, the compounds of the invention have antiproliferative activity, specifically, they inhibit cell division in G2/M phase of the cell cycle.

DETAILED DESCRIPTION OF THE INVENTION

The invention relates to substituted pyrroles. More particularly, the invention relates to substituted pyrroles of the formula

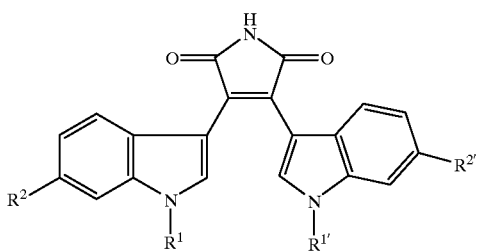

wherein
- $R^1$ and $R^{1'}$ are independently hydrogen, lower alkyl, lower alkenyl or lower alkynyl;
- $R^2$ is hydrogen, nitro, cyano, halogen, lower alkyl, lower alkenyl, lower alkynyl, or lower alkoxy; and
- $R^{2'}$ is a heteroaryl, heterocycle, ethyl substituted with a heteroaryl, or ethoxy substituted with a heteroaryl or heterocycle; or a pharmaceutically acceptable salt thereof.

As used herein, the term "lower alkyl", alone or in combination, means a straight or branched chain alkyl group containing a maximum of 3 carbon atoms, such as methyl, ethyl, propyl, and isopropyl, which is unsubstituted or substituted by one or more of hydroxy, lower alkoxy, amino, halogen, thio-lower alkyl or lower alkylsulphinyl. Examples of lower alkyl substituted by one or more halogen includes chloromethyl and triflouromethyl.

The term "lower alkoxy", alone or in combination, means a group wherein the lower alkyl residue is defined as above, for example, methoxy, ethoxy, propoxy, isopropoxy and the like.

The term "heteroaryl", alone or in combination, means a 5 or 6 membered aromatic ring containing 1 to 4 heteroatoms which may the same or different, and where the ring is unsubstituted or substituted by one or more of halogen, lower alkyl, hydroxy, carboxy, lower alkoxy, nitro, amino or cyano. The heteroatom(s) are selected from the group consisting of nitrogen, sulfur and oxygen. Examples of heteroaryl are furan, thiophene, pyrrole, oxazole, thiazole, imidazole, pyrazole, isoxazole, isothiazole, oxadiazole, triazole, tetrazole, thiadiazole, pyridine, pyridazine, pyrimidine, pyrazine, and triazine.

The term "heterocycle", alone or in combination, means a 4 to 7 membered non-aromatic ring containing one or more heteroatoms which may be the same or different, and where the ring is partially or completely saturated and where the ring is unsubstituted or substituted by one or more of halogen, lower alkyl, hydroxy, carboxy, lower alkoxy, nitro, amino or cyano. The heteroatom(s) are selected from the group consisting of nitrogen, sulfur and oxygen. Examples of unsubstituted heterocycle are pyrroline, pyrrolidine, imidazoline, imidazolidine, pyrazoline, pyrazolidine, pyran, piperidine, dioxane, morpholine, dithiane, thiomorpholine, piperazine, and trithiane.

The term "halogen" means flourine, chlorine, bromine or iodine.

The term "amino" means an unsubstituted amine group or an amine substituted by one or more substituents selected from alkyl, aryl, acyl, alkylsulfonyl or arylsulfonyl, The term "alkenyl" means a straight or branched chain hydrocarbon group of 2 to 5 carbon atoms having at least one double bond.

The term "alkynyl" means a straight or branched chain hydrocarbon group of 2 to 5 carbon atoms having at least one triple bond.

In formula I above, preferably, $R^1$ and $R^{1'}$ are independently hydrogen, methyl or ethyl, which are unsubstituted or substituted by lower alkoxy, preferably methoxy or ethoxy. Most preferably, at least one of $R^1$ and $R^{1'}$ is lower alkyl, most preferably unsubstituted methyl.

Preferably, when $R^2$ is lower alkoxy, it is methoxy or ethoxy, most preferably methoxy. Preferably, when $R^2$ is lower alkyl, it is methyl or ethyl, which is unsubstituted or substituted by one or more of lower alkoxy or halogen. Most preferred when $R^2$ is lower alkyl it is methyl, which is w i substituted or substituted by methoxy. $R^2$ may also preferably be haloalkyl such as trifluoromethyl.

When $R^{2'}$ is heteroaryl, it is preferably thiophenyl, furanyl, imidazolyl which is unsubstituted or substituted with lower alkyl, thiazolyl, pyrazolyl which is unsubstituted or substituted with lower alkyl, pyrimdinyl, or isothiazolyl.

When $R^{2'}$ is is heterocycle, it is preferably unsubstituted morpholine, unsubstituted pyrrolidine, unsubstituted piperidine, or piperazine which is unsubstituted or substituted with lower alkyl, lower alkoxy or carboxy.

When $R^{2'}$ is ethyl substituted with heteroaryl, preferably the heteroaryl is imidazole. In addition, $R^{2'}$ may be methyl or propyl substituted with a heteroaryl.

In addition to ethoxy substituted with a heteroaryl or heterocycle, $R^{2'}$ may also be methoxy or propoxy substituted with a heteroaryl or heterocycle.

In a preferred embodiment, when $R^{2'}$ is thiophenyl, preferably $R^1$ and $R^{1'}$ are both methyl and $R^2$ is hydrogen or nitro.

In another preferred embodiment, when $R^{2'}$ is furanyl, preferably $R^1$ is hydrogen, methyl, $R^{1'}$ is methyl, and $R^2$ is hydrogen or nitro.

In another preferred embodiment, when $R^{2'}$ is imidazolyl which is unsubstituted or substituted with lower alkyl, preferably, methyl, preferably $R^1$ is methyl $R^{1'}$ is methyl and $R^2$ is hydrogen, nitro, cyano, halogen or methoxy.

In another preferred embodiment, when $R^{2'}$ is thiazolyl, preferably $R^1$ and $R^{1'}$ are both methyl and $R^2$ is hydrogen or nitro.

In another preferred embodiment, when $R^{2'}$ is pyrazolyl which is unsubstituted or substituted with lower alkyl, preferably methyl, preferably $R^1$ and $R^{1'}$ are both methyl and $R^2$ is hydrogen, nitro or halogen.

In another preferred embodiment, when $R^{2'}$ is pyrimdinyl, preferably $R^1$ and $R^{1'}$ is methyl and $R^2$ is hydrogen or nitro.

In another preferred embodiment, when $R^{2'}$ is isothiazole, preferably $R^1$ and $R^1$ is methyl and $R^2$ is hydrogen or nitro.

In another preferred embodiment, when $R^{2'}$ is pyrrolidinyl, preferably, $R^1$ is hydrogen or methyl, $R^1$ is hydrogen, methyl or methoxymethyl, and $R^2$ is hydrogen, nitro, cyano, halogen, trifluoromethyl, or methoxy.

In another preferred embodiment, when $R^{2'}$ is piperidinyl, preferably $R^1$ and $R^{1'}$ are both methyl and $R^2$ is hydrogen.

In another preferred embodiment, when $R^{2'}$ is morpholinyl, preferably $R^1$ is hydrogen, methyl, preferably $R^1$ is methyl, hydrogen or methoxymethyl, and $R^2$ is hydrogen, nitro, cyano, halogen, methyl, trifluoromethyl, or methoxy.

In another preferred embodiment, when $R^{2'}$ is ethoxy substituted by a heteroaryl or a heterocycle, preferably a heteroaryl and more preferably imidazolyl, preferably $R^1$ and $R^{1'}$ are both methyl and $R^2$ is nitro.

The compounds of formula I are prepared as follows.

The starting material, a compound of formula 4 can be prepared according to Scheme 1

SCHEME 1

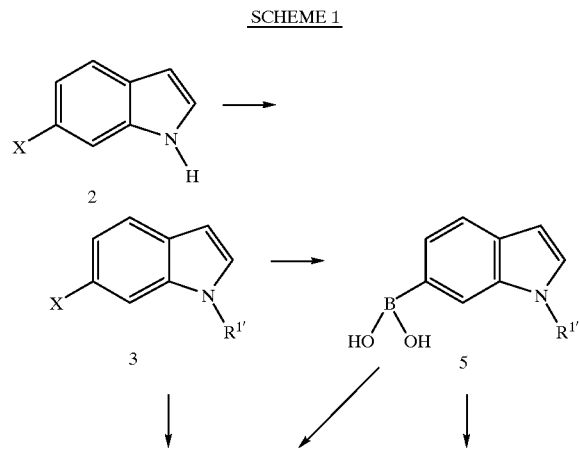

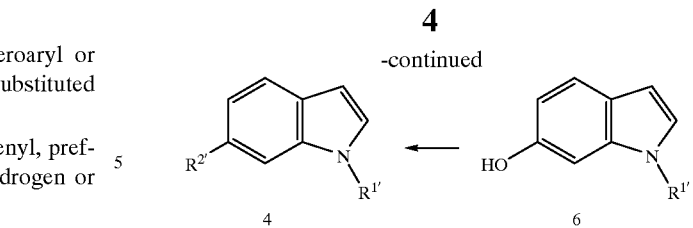

When $R^{2'}$ is heterocycle or heteroaryl and $R^1$ is lower alkyl, compound 4 can be prepared according to Scheme 1.

A compound of formula 2, wherein X represents Br or I, is prepared by known methods (Moyer, M. P.; Shiurba, J. F.; Rapoport, H. *J. Org. Chem.* 1986, 51, 5106.), and is alkylated by known methods (NaH and alkyl iodide in N,N-dimethylformamide (DMF) or tetrahydrofuran at 0° C. to about 25° C.) to give a corresponding compound of formula 3. Alternatively, alkylation can be carried out using dimethyl carbonate and a base (such as $K_2CO_3$) or a catalyst (such as TBAB) in DMF, by heating the reaction mixture to reflux (greater than 90° C.).

A compound of formula 3 is reacted with a heteroaryl substituted trialkylstnnane, in a solvent such as toluene or THF in the presence of a base, such as triethylamine, catalyzed by a palladium catalyst, such as tetrakis (triphenylphosphine) palladium (0) at a temperature of 50° C. to reflux to afford a corresponding compound of formula 4 with $R^{2'}$ being heteroaryl.

Alternatively, a compound of formula 3 is reacted with imidazole or substituted imidazole, in the presence of cesium carbonate, 1,10-phenanthroline and dibenzylideneacetone, catalyzed by copper(I) trifluoromethanesulfonate benzene complex, in a solvent such as xylene, at a temperature of 110–125° C. to afford a corresponding compound of formula 4 with $R^{2'}$ being the imidazolyl with the nitrogen attached at the indole ring, as described in Kiyoori, A.; Marcoux, J-F.; Buchwald, S. L. *Tetrahedron letters,* 1999, 40, 2657.

When $R^{2'}$ is a heterocyclic amine such as pyrrolidinyl or morpholinyl, a compound of formula 4 can be prepared from a compound of formula 3 using Buchwald reaction. [Wolfe, J. P.; Buchwald, S. L. *J. Org. Chem.* 1997, 62, 6066.] A compound of formula 3 is reacted with a heterocyclic amine, such as pyrrolidine, in the presence of sodium t-butoxide, 2,2'-bis(diphenylphosphino)-1,1'-binaphthyl and 18-crown-6, catalyzed by tris(dibenzylideneacetone) dipalladium (0) in a solvent such as tetrahydrofuran, at a temperature of 25° C. to 65° C. to afford a compound of formula 4.

When $R^{2'}$ is pyrimidinyl, a compound of formula 4 is prepared by the following sequence:

A compound of formula 3 is reacted with n-butyllithium at −78° C. in tetrahydrofuran followed by trialkylborate. The resulting product is then treated with aqueous methanol to give a compound of formula 5.

A compound of formula 5 is reacted with bromopyrimidine, tetrakis(triphenylphosphine) palladium (0) in the presence of a base such as sodium carbonate in dioxane at a temperature of 100°–110° C. to give a compound of formula 4 with $R^{2'}$ being pyrimidinyl.

When $R^{2'}$ is ethoxy substituted heterocycle or heteroaryl, such as 2-imidazol-1-yl-ethoxy, compound of formula 4 can be prepared by the following sequence:

A compound of formula 5 is reacted with hydrogen peroxide and sodium hydroxide to give compound 6. Treatment of compound 6 with 1-(2-hydroxyethyl)imidazol, triphenylphosphine and diethyl azodicarboxylate results in a compound of formula 4 with $R^{2'}$ being 2-imidazol-1-yl-ethoxy.

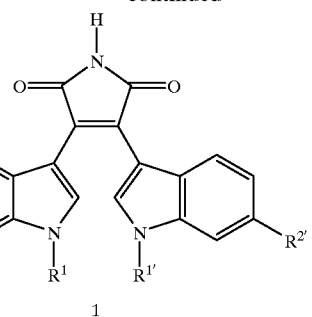

1

A compound with formula 1 may be prepared according to Scheme 2, provided that when $R^2$ and $R^1$ are substituents which react with acid chlorides, such as, for example, alkyl amine, such substituent is protected with a conventional protecting group.

A compound of formula 4 is reacted with oxalyl chloride in a solvent such as diethyl ether or dichloromethane at a temperature of from 0° C. to 25° C. to form a corresponding compound of formula 7.

A compound of formula 7 is reacted with a compound of formula 8, a known compound (U.S. Pat. No. 5,057,614) or a compound prepared by known methods, in the presence of a base, such as triethylamine in dichloromethane at a temperature between 0° C. to 25° C. The resultant product is then treated with an acid, such as p-toluenesulfonic acid or hydrochloric acid in a solvent such as methylene chloride, methanol or THF at a temperature of 25° C. to 65° C. to form a corresponding compound of formula 1. If a protecting group was utilized during the reaction of 7 and 8, it is removed at this point using methods known in the art.

SCHEME 2

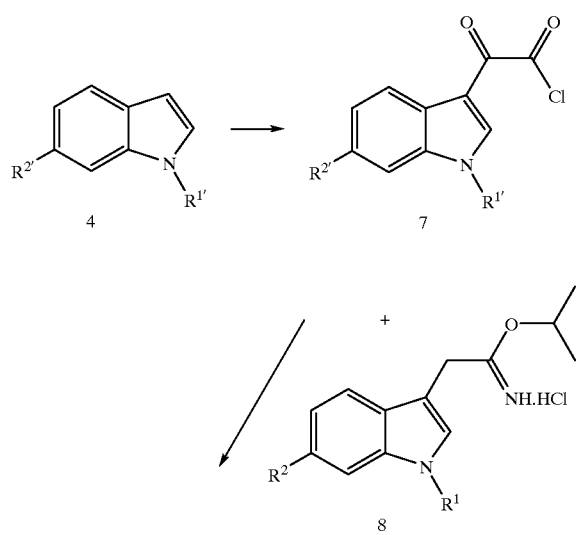

SCHEME 3

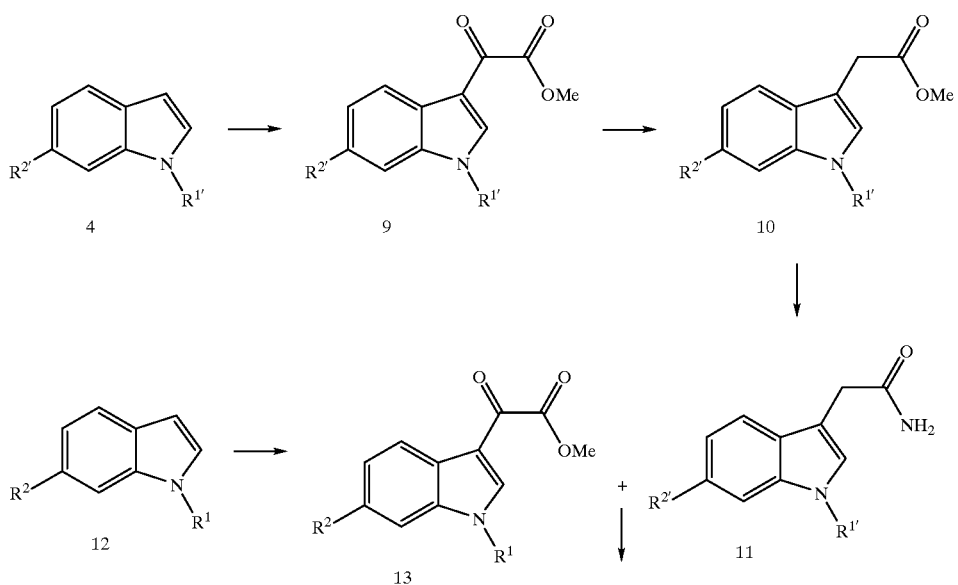

-continued

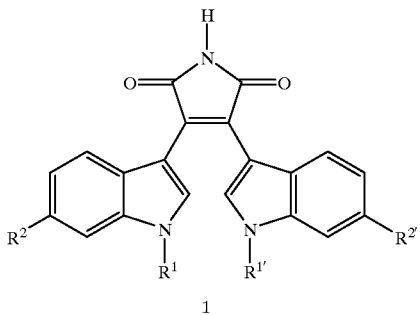

1

As set forth in Scheme 3, a compound of formula 4 is reacted with methyl oxalyl chloride in a solvent, such as diethyl ether or dichloromethane or without a solvent, at a temperature of 0° C. to 25° C. to form a compound of formula 9.

A compound of formula 9 is reacted with sodium hypophosphite hydrate, catalyzed by palladium on charcoal in a solvent such as dioxane at a temperature of 100° C. to 110° to afford a compound of formula 10.

A compound of formula 10 is reacted with ammonium hydroxide to give a corresponding compound of formula 11.

A compound of formula 12 is reacted with methyl oxalyl chloride in a solvent, such as diethyl ether or dichloromethane or without a solvent, at a temperature of 0° C. to 25° C. to form a compound of formula 13.

A compound of formula 11 is reacted with a compound of formula 13 in the presence of a base, such as potassium t-butoxide, in a solvent such as tetrahydrofuran at a temperature of 0° C. to 25° C. The resulting product is then treated with an acid, such as hydrochloric acid to give a compound of formula 1.

SCHEME 4

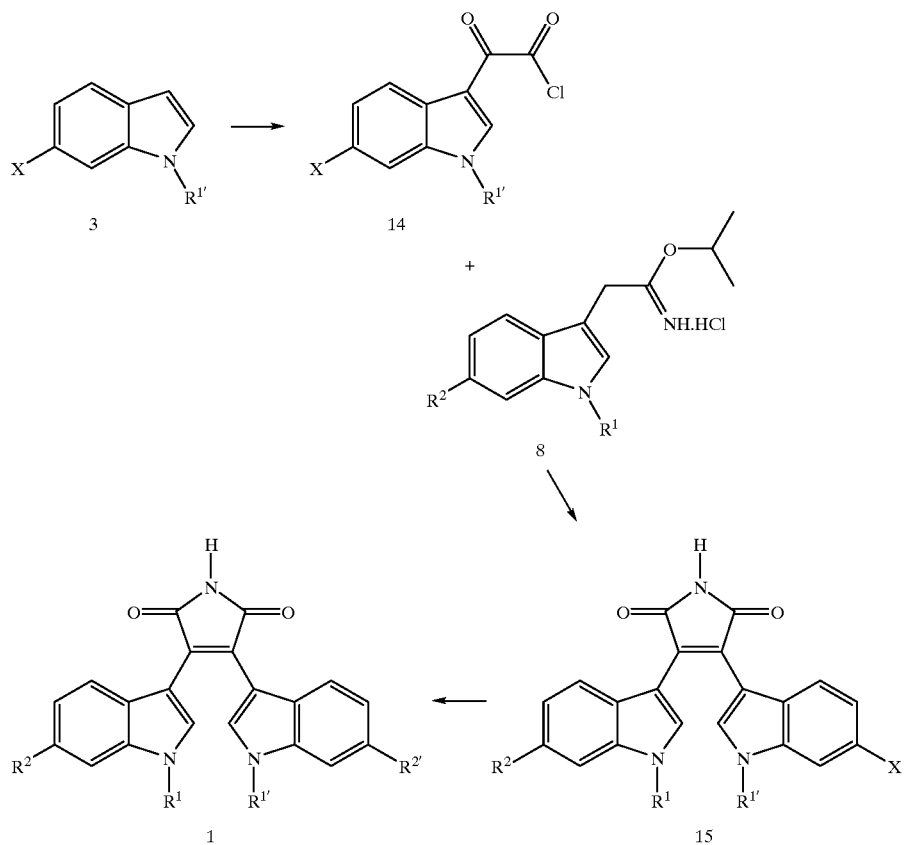

As set forth in Scheme 4, a compound with formula 3 is reacted with oxalyl chloride in a solvent such as diethyl ether or methylene chloride, at a temperature of 0° C. to 25° C. to afford a compound of formula 14.

A compound of formula 14 is reacted with a compound of formula 8 in the presence of a base, such as triethylamine in methylene chloride at a temperature between 0° C. and 25° C. The resultant product is then treated with an acid, such as p-toluenesulfonic acid or hydrochloric acid in a solvent such as methylene chloride, methanol or THF at a temperature of 25° C. to 65° C. to form a compound of formula 15.

A compound with a formula 15 is reacted with a heteroaryl substituted trialkyistannane or boronic acid such as 2-(tributylstannyl) thiophene, or 2-(tributylstannyl) thioazole, thiophene-3-boronic acid, in the presence of a base such as triethylamine or sodium carbonate, catalyzed by a palladium catalyst such as tetrakis(triphenylphosphine)palladium (0), or tri(dibenzylideneacetolne)dipalladium (0), in a solvent such as toluene, acetonitrile, tetrahydrofuran, or dioxane, at a temperature of 80° C. to 110° C. to afford a compound with formula 1.

The conversion of an acidic compound of formula I into a pharmaceutically acceptable salt can be carried out by treatment with a suitable base in a known manner. Suitable salts are those derived not only from inorganic bases, for example, sodium, potassium or calcium salts, but also from organic bases such as ethylenediamine, monoethanolamine or diethanolamine. The conversion of a basic compound of formula I into a pharmaceutically acceptable salt can be carried out by treatment with a suitable acid in a known manner. Suitable salts arc those derived not only from inorganic acids, for example, hydrochlorides, hydrobromides, phosphates or sulphates, but also from organic acids, for example, acetates, citrates, fumarates, tartrates, maleates, methansulphonates or p-toluenesulphonates.

The antiproliferatiave activity of the compounds of the invention is demonstrated below. These effects indicate that the compounds of the present invention are useful in treating cancer, in particular solid tumors such as breast and colon tumors.

The epithelial breast carcinoma cell line (MDAMB-435) was purchased from ATCC (American Type Cell Culture Collection) and was grown in culture medium as recommended by ATCC. For analysis of the effect of various compounds of formula I on the growth of these cells, the cells were plated at a concentration of 1500 cells/well in a 96 well tissue culture plate ("test plate"). The day after the cells were plated, the compounds to be analyzed were dissolved in 100% DMSO (dimethyl sulfoxide) to yield at 10 mM stock solution. Each compound was diluted in $H_2O$ to 1 mM and was added to triplicate wells in the first row of a 96 well master plate containing medium to yield a final concentration of 40 $\mu$M. The compounds were then serially diluted in medium in the "master plate". The diluted compound(s) were then transferred to test plates containing cells. A row of vehicle "control cells" received DMSO. The final concentration of DMSO in each well was 0.1%. 5 days post drug addition, the plate was analyzed as described below.

MTT (3-(4-5 methyl thiazole-2-yl)-2,5-diphenyl tetrazolium bromide; thiazolyl blue) was added to each well to yield a final concentration of 1 mg/ml. The plate was then incubated at 37° C. for 2½–3 hours. The MTT-containing medium was then removed and 50 $\mu$l of 100% ethanol was added to each well to dissolve the formazan. The absorbences were then read using an automated plate reader (Bio-tek microplate reader). $IC_{50}$s were calculated using the Reed and Munsch equation, see Am. J. Hygiene Vol. 27 pgs. 493–497, 1938.

The results of the foregoing in vitro experiments are set forth in Table I below.

TABLE I

| Example | $R^1$ | $R^{1'}$ | $R^2$ | $R^{2'}$ | $IC_{50}$ ($\mu$M) |
|---------|-------|----------|-------|----------|--------------------|
| 12d | $CH_3$ | $CH_3$ | $NO_2$ | 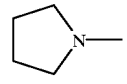 | 0.002 |
| 12h | $CH_3$ | H | $NO_2$ | 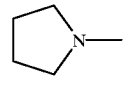 | 0.002 |
| 12e | $CH_3$ | H | F | 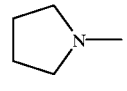 | 0.003 |
| 12f | $CH_3$ | H | Cl | 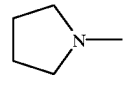 | <0.003 |
| 12g | $CH_3$ | $CH_2OCH_3$ | $NO_2$ | 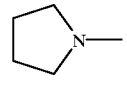 | 0.02 |
| 14f | $CH_3$ | $CH_3$ | Br | 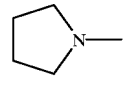 | 0.005 |

TABLE I-continued
| Example | R¹ | R¹' | R² | R²' | IC$_{50}$ ($\mu$M) |
|---|---|---|---|---|---|
| 14g | CH$_3$ | CH$_3$ | OCH$_3$ | 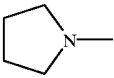 | 0.04 |
| 14h | CH$_3$ | CH$_3$ | CF$_3$ | 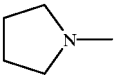 | 0.08 |
| 12j | CH$_3$ | CH$_3$ | H | 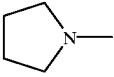 | 0.06 |
| 15 | CH$_3$ | CH$_3$ | CN | 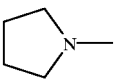 | <0.01 |
| 12l | CH$_3$ | CH$_3$ | H | 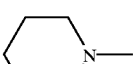 | 0.23 |
| 12a | CH$_3$ | CH$_3$ | NO$_2$ | 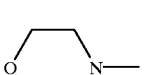 | <0.01 |
| 11 | CH$_3$ | CH$_3$ | H | 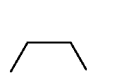 | 0.02 |
| 13 | CH$_3$ | CH$_3$ | CN | 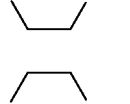 | 0.004 |
| 14a | CH$_3$ | CH$_3$ | OCH$_3$ | 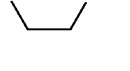 | 0.02 |
| 14b | CH$_3$ | CH$_3$ | F | 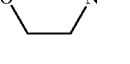 | 0.03 |
| 14c | CH$_3$ | CH$_3$ | Cl | 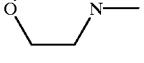 | 0.002 |
| 14d | CH$_3$ | CH$_3$ | Br | 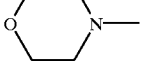 | 0.003 |
| 14e | CH$_3$ | CH$_3$ | CF$_3$ | 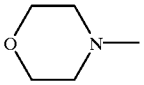 | 0.05 |
| 12b | CH$_3$ | CH$_3$ | CH$_3$ | 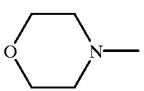 | <0.01 |

TABLE I-continued
| Example | R¹ | R¹' | R² | R²' | IC$_{50}$ ($\mu$M) |
|---|---|---|---|---|---|
| 12c | H | CH$_3$ | H | 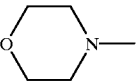 | 0.07 |
| 3 | CH$_3$ | CH$_3$ | H | 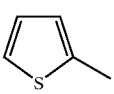 | 0.04 |
| 5 | CH$_3$ | CH$_3$ | H | 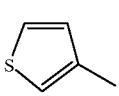 | 0.04 |
| 2g | CH$_3$ | CH$_3$ | H | 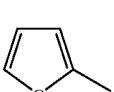 | 0.02 |
| 2i | H | CH$_3$ | H | 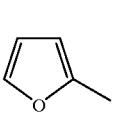 | 0.03 |
| 2h | CH$_3$ | CH$_3$ | NO$_2$ |  | 0.01 |
| 4a | CH$_3$ | CH$_3$ | H | 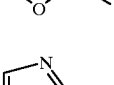 | 0.024 |
| 2c | CH$_3$ | CH$_3$ | NO$_2$ | 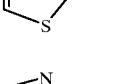 | 0.03 |
| 4b | CH$_3$ | CH$_3$ | H | 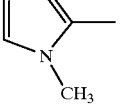 | 0.06 |
| 4c | CH$_3$ | CH$_3$ | NO$_2$ | 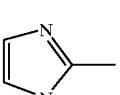 | 0.02 |
| 4d | CH$_3$ | CH$_3$ | NO$_2$ | 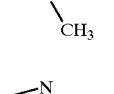 | 0.02 |
| 6 | CH$_3$ | CH$_3$ | NO$_2$ | 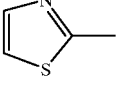 | 0.04 |
| 1 | CH$_3$ | CH$_3$ | NO$_2$ | 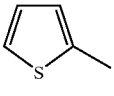 | 0.005 |

TABLE I-continued

| Example | R$^1$ | R$^{1'}$ | R$^2$ | R$^{2'}$ | IC$_{50}$ ($\mu$M) |
|---|---|---|---|---|---|
| 2a | CH$_3$ | CH$_3$ | H | 1-methyl-1H-imidazol-5-yl | 0.05 |
| 2b | CH$_3$ | CH$_3$ | OCH$_3$ | 1-methyl-1H-imidazol-5-yl | 0.06 |
| 2d | CH$_3$ | CH$_3$ | NO$_2$ | 1-ethyl-2-methyl-1H-imidazol-5-yl | 0.12 |
| 2e | CH$_3$ | CH$_3$ | H | 1H-imidazol-4-yl | 0.08 |
| 2o | CH$_3$ | CH$_3$ | NO$_2$ | 1H-imidazol-4-yl | 0.04 |
| 2f | CH$_3$ | CH$_3$ | NO$_2$ | 1H-imidazol-4-yl | 0.02 |
| 7 | CH$_3$ | CH$_3$ | H | 1H-imidazol-1-yl | 0.06 |
| 8a | CH$_3$ | CH$_3$ | NO$_2$ | 1H-imidazol-1-yl | 0.03 |
| 9 | CH$_3$ | CH$_3$ | OCH$_3$ | 1H-imidazol-1-yl | 0.06 |
| 10a | CH$_3$ | CH$_3$ | Br | 1H-imidazol-1-yl | 0.025 |
| 10b | CH$_3$ | CH$_3$ | CN | 1H-imidazol-1-yl | 0.03 |
| 8b | CH$_3$ | CH$_3$ | NO$_2$ | 2-methyl-1H-imidazol-1-yl | 0.25 |

TABLE I-continued
| Example | R¹ | R¹' | R² | R²' | IC$_{50}$ ($\mu$M) |
|---|---|---|---|---|---|
| 8c | CH$_3$ | CH$_3$ | NO$_2$ | 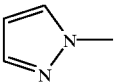 | 0.02 |
| 8d | CH$_3$ | CH$_3$ | H | 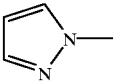 | 0.03 |
| 8e | CH$_3$ | CH$_3$ | Br | 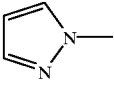 | 0.025 |
| 2j | CH$_3$ | CH$_3$ | NO$_2$ | 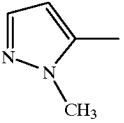 | 0.02 |
| 2k | CH$_3$ | CH$_3$ | H | 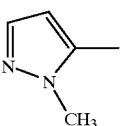 | 0.25 |
| 2l | CH$_3$ | CH$_3$ | Br | 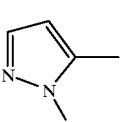 | 0.07 |
| 17 | CH$_3$ | CH$_3$ | NO$_2$ | 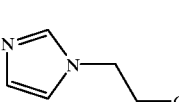 | 0.07 |
| 2m | CH$_3$ | CH$_3$ | NO$_2$ | 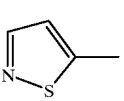 | 0.01 |
| 2n | CH$_3$ | CH$_3$ | H | 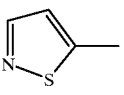 | 0.04 |
| 18 | CH$_3$ | CH$_3$ | NO$_2$ | 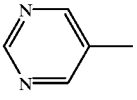 | 0.05 |
| 19 | CH$_3$ | CH$_3$ | H | 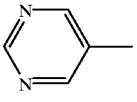 | 0.08 |
| 12i | H | CH$_3$ | H | 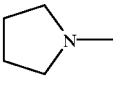 | 0.08 |
| 14i | CH$_3$ | CH$_3$ | Cl | 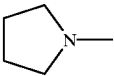 | 0.01 |

TABLE I-continued

| Example | R¹ | R¹' | R² | R²' | IC$_{50}$ ($\mu$M) |
|---|---|---|---|---|---|
| 12m | CH$_3$ | CH$_3$OCH$_2$ | F | 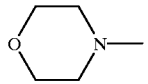 | 0.17 |
| 12n | CH$_3$ | H | F | 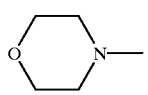 | 0.012 |
| 12o | CH$_3$ | H | H | 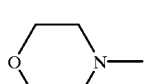 | 0.037 |
| 16 | CH$_3$ | CH$_3$ | CH$_3$OCH$_2$ | 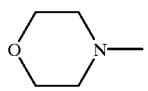 | 1.18 |
| 12k | CH$_3$ | CH$_3$ | H | 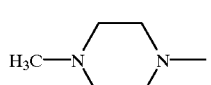 | 3.41 |

In an alternative embodiment, the present invention is directed to pharmaceutical compositions comprising at least one compound of formula I or a pharmaceutically acceptable salt thereof.

These pharmaceutical compositions can be administered orally, for example, in the form of tablets, coated tablets, dragees, hard or soft gelatin capsules, solutions, emulsions or suspensions. They can also be administered rectally, for example, in the form of suppositories. In particular, however, the compounds of the present invention are suitable for parenteral administration, for example, in the form of injection solutions.

The pharmaceutical compositions of the present invention comprising compounds of formula I, prodrugs of such compounds, or the salts thereof, may be manufactured in a manner that is known in the art, e.g. by means of conventional mixing, encapsulating, dissolving, granulating, emulsifying, entrapping, dragee-making, or lyophilizing processes. These pharmaceutical preparations can be formulated with therapeutically inert, inorganic or organic carriers. Lactose, corn starch or derivatives thereof, talc, steric acid or its salts can be used as such carriers for tablets, coated tablets, dragees and hard gelatin capsules. Suitable carriers for soft gelatin capsules include vegetable oils, waxes and fats. Depending on the nature of the active substance, no carriers are generally required in the case of soft gelatin capsules. Suitable carriers for the manufacture of solutions and syrups are water, polyols, saccharose, invert sugar and glucose. Suitable carriers for injection are water, alcohols, polyols, glycerine, vegetable oils, phospholipids and surfactants. Suitable carriers for suppositories are natural or hardened oils, waxes, fats and semi-liquid polyols.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances, including additional active ingredients other than those of formula I.

As mentioned above, the compounds of the present invention are useful in the treatment or control of cell proliferative disorders, in particular oncological disorders. These compounds and formulations containing said compounds are particularly useful in the treatment or control of solid tumors, such as, for example, breast and colon tumors.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and will be adjusted to the individual requirements in each particular case. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

EXAMPLES

The compounds of the present invention may be synthesized according to known techniques, such as, for example, the general schemes provided above. The following examples illustrate preferred methods for synthesizing the compounds and formulations of the present invention.

Example 1

3-[1-Methyl-6-(3-methyl-3H-imidazol-4-yl)-1H-indol-3-yl]-4-(1-methyl-6-nitro-1H-indol-3-yl)-pyrrole-2,5-dione a) 6-Bromoindole (10.4 g, 53.1 mmol) (prepared according to Moyer, M. P.; Shiurba, J. F.; Rapoport, H. *J. Org. Chem.* 1986, 51, 5106.) was added in small portions over 30 min to a stirred suspension of sodium hydride (2.96 g, 61.7 mmol, 50% in mineral oil) in dry THF (120 mL) at 0° C. Stirring was continued for another 30 min. Iodomethane (4.5 ml, 71.6 mmol) was added dropwise. After 1 h, the mixture was poured into ice-water and extracted with ether (3×200 mL). The combined organic extracts were washed with brine and dried (MgSO$_4$). Evaporation of the solvents and chromatography of the residue over silica gel using hexane gave 6-bromo-1-methyl-1H-indole (10.8 g, 97%).

b) A solution of 6-bromo-1-methyl-1H-indole (6.2 g, 29.5 mmol) in toluene was degassed by bubbling argon through the solution for 10–20 min. Et$_3$N (8.2 mL, 59 mmol), tetrakis(triphenylphosphine)palladium (0) (681 mg, 0.59 mmol) and 1-methyl-5-(tributylstannyl)imidazole (Gaare, K.; Repstad, T.; Benneche, T.; Undheim, K. Acta Chem. Scan. 1993, 47, 57.) (11.6 g, 31.2 mmol) in toluene (30 mL) were added and the mixture was heated to 120° C. for 18 h until Pd black appeared. The mixture was cooled, filtered through a pad of silica gel and the pad was washed well with EtOAc. The filtrate was evaporated and chromatography of the residue over silica gel using 0.5–1% methanol in EtOAc gave 1-methyl-6-(3-methyl-3H-imidazol-4-yl)-1H-indole (5.21 g, 84%) as an off white crystalline solid.

c) 1-Methyl-6-(3-methyl-3H-imidazol-4-yl)-1H-indole (5.0 g, 23.7 mmol) was dissolved in CH$_2$Cl$_2$ (25 mL) (dried under 3A° molecular sieves) at 0° C. A solution of oxalyl chloride in CH$_2$Cl$_2$ (2 M, 23.7 mL, 47.4 mmol) was added dropwise over 10 min. The mixture was stirred at 0° C. for 2.5 h and evaporated. Ether (25 mL) was added to the solid residue and the mixture was stirred for 30 min. The resulting yellow solid was filtered off, washed with ether and dried under vacuum for 30 min. 2-(1-Methyl-6-nitro-1H-indol-3-yl)acetimidic acid isopropyl ester hydrochloride (7.02 g, 22.5 mmol) and CH$_2$Cl$_2$ (200 mL) were added to the yellow solid at 0° C. Et$_3$N (dried over 3A° molecular sieves) (16.5 mL, 118.6 mmol) was added dropwise over 10 min., and the orange-red mixture was stirred at room temperature overnight. The mixture was diluted with CHCl$_3$ and washed with aqueous Na$_2$CO$_3$. The aqueous layer was back extracted with CHCl$_3$. The combined organic extracts were washed with brine, dried (K$_2$CO$_3$) and evaporated. MeOH (150 mL) and concentrated HCl (37%, 10 mL) were added. The mixture was heated at reflux for 2 h, then cooled, diluted with CHCl$_3$ and washed with aqueous Na$_2$CO$_3$. The aqueous layer was back extracted with CHCl$_3$. The combined organic extracts were washed with brine and dried (K$_2$CO$_3$). The mixture was passed through a pad of silica gel (10×10 cm) and the pad was washed with 10% methanol/EtOAc. Evaporation of the combined filtrates gave the crude product as an orange solid. Crystallization of the product from EtOH/CHCl$_3$ gave 3-[1-methyl-6-(3-methyl-3H-imidazol-4-yl)-1H-indol-3-yl]-4-(1-methyl-6-nitro-1H-indol-3-yl)pyrrole-2,5-dione (5.65 g, 49%) as an orange solid.

Example 2

In a manner similar to that described in Example I, the following compounds were prepared. The starting materials were prepared in a manner analogous to that described in 1(a) and 1(b).

a) 3-(1-Methyl-1H-indol-3-yl)-4-[1-methyl-6-(3-methyl-3H-imidazol-4-yl)-1H-indol -3-yl]pyrrole-2,5-dione (391 mg, 45%) was prepared as an orange solid using 1-methyl-6-(3-methyl-3H-imidazol-4-yl)-1H-indole (422 mg, 2 mmol) and 1-methyl-3-indoleacetimidic acid isopropyl ester hydrochloride (530 mg, 2 mmol).

b) 3-(6-Methoxy-1-methyl-1H-indol-3-yl)-4-[1-methyl-6-(3-methyl-3H-imidazol-4-yl)-1H-indol-3-yl]pyrrole-2,5-dione (78 mg, 11%) was prepared as a dark brown solid using 1-methyl-6-(3-methyl-3H-imidazol-4-yl)-1H-indole (316 mg, 1.5 mmol) and 2-(1-methyl-6-methoxy-1H-indol-3-yl)acetimidic acid isopropyl ester hydrochloride (445 mg, 1.5 mmol).

c) 3-[1-Methyl-6-(1-methyl-1H-imidazol-2-yl)-1H-indol-3-yl]-4-(1-methyl-6-nitro-1H-indol-3-yl)pyrrole-2,5-dione (1.08 g, 34%) was prepared as an orange solid from 6-(1-methyl-1H-imidazol-2-yl)-1-methyl-1H-indole and 2-(1-methyl-6-nitro-1H-indol-3-yl)acetimidic acid isopropyl ester hydrochloride.

d) 3-[6-(1-Ethyl-1H-imidazol-2-yl)-1H-indol-3-yl]-4-(1-methyl-6-nitro-1H-indol-3-yl)pyrrole-2,5-dione (155 mg, 38%) was prepared using 6-(1-ethyl-1H-imidazol-2-yl)-1-methyl-1H-indole (185 mg, 0.82 mmol) and 2-(1-methyl-6-nitro-1H-indol-3-yl)acetimidic acid isopropyl ester hydrochloride (256 mg, 0.82 mmol).

e) 3-[6-(1H-Imidazol-2-yl)-1-methyl-1H-indol-3-yl]-4-(1-methyl-1H-indol-3-yl)pyrrole-2,5-dione (37 mg, 14%) was prepared as an orange solid using 1-methyl-6-[1-(2-trimethylsilanyl-ethoxymethyl)-1H-imidazol-2-yl]-1H-indole (200 mg, 0.61 mmol) and 1-methyl-3-indoleacetimidic acid isopropyl ester hydrochloride (162 mg, 0.61 mmol) followed by deprotection using 20% HCl in refluxing EtOH.

f) 3-[6-(3H-Imidazol-4-yl)-1-methyl-1H-indol-3-yl]-4-(1-methyl-6-nitro-3-yl)pyrrole-2,5-dione hydrochloride (45 mg, 18%) was prepared from 1-methyl-6-[3-(2-trimethylsilanyl-ethoxymethyl)-3H-imidazol-4-yl]-1H-indole (160 mg, 0.49 mmol) and 2-(1-methyl-6-nitro-1H-indol-3-yl)acetimidic acid isopropyl ester hydrochloride (156 mg, 0.5 mmol) followed by deprotection using 20% HCl in refluxing EtOH.

g) 3-(6-Furan-2-yl-1-methyl-1H-indol-3-yl)-4-(1-methyl-1H-indol-3-yl)pyrrole-2,5-dione (51 mg, 27%) was prepared as an orange solid using 6-furan-2-yl-1-methyl-1H-indole (100 mg, 0.5 mmol) and 1-methyl-3-indoleacetimidic acid isopropyl ester hydrochloride (120 mg, 0.45 mmol).

h) 3-(6-Furan-2-yl-1-methyl-1H-indol-3-yl)-4-(1-methyl-6-nitro-1H-indol-3-yl)pyrrole-2,5-dione (70 mg, 40%) was prepared using 6-furan-2-yl-1-methyl-1H-indole (100 mg, 0.5 mmol) and 2-(1-methyl-6-nitro-1H-indol-3-yl) acetimidic acid isopropyl ester hydrochloride (117 mg, 0.38 mmol).

i) 3-(6-Furan-2-yl-1-methyl-1H-indol-3-yl)-4-(1H-indol-3-yl)pyrrole-2,5-dione was prepared from 6-furan-2-yl-1-methyl-1H-indole and 2-[1-(2,2-dimethylpropionyl)-1 H-indol-3-yl]acetimidic acid isopropyl ester hydrochloride followed by deprotection with NaOMe in methanol.

j) 3-[1-Methyl-6-(2-methyl-2H-pyrazol-3-yl)-1H-indol-3-yl]-4-(1-methyl-6-nitro-1H-indol-3-yl)pyrrole-2,5-dione was prepared from 1-methyl-6-(2-methyl-2H-pyrazol-3-yl)-1H-indole and 2-(1-methyl-6-nitro-1H-indol-3-yl) acetimidic acid isopropyl ester hydrochloride.

k) 3-(1-Methyl-1H-indol-3-yl)-4-[1-methyl-6-(2-methyl-2H-pyrazol-3-yl)-1H-indol-3-yl]pyrrole-2,5-dione was prepared from 1-methyl-6-(2-methyl-2-H-pyrazol-3-yl)-1H-indole and 2-(1-methyl-1H-indol-3-yl)acetimidic acid isopropyl ester hydrochloride.

l) 3-(6-Bromo-1-methyl-1H-indol-3-yl)-4-[1-methyl-6-(2-methyl-2H-pyrazol-3yl)-1H-indol-3-yl]pyrrole-2,5-dione was prepared from 1-methyl-6-(2-methyl-2H-pyrazol-3-yl)-1H-indole and 2-(6-bromo-1 -methyl-1H-indol-3 -yl) acetimidic acid isopropyl ester hydrochloride.

m) 3-(6-Isothiazol-5-yl-1-methyl-1H-indol-3-yl)-4-(1-methyl-6-nitro-1H-indol-3-yl)pyrrole-2,5-dione was prepared from 6-isothiazol-5-yl-1-methyl-1H-indole and 2-(1-methyl-6-nitro-1H-indol-3-yl)-acetimidic acid isopropyl ester hydrochloride.

n) 3-(6-Isothiazol-5-yl-1-methyl-1H-indol-3-yl)-4-(1-methyl-1H-indol-3-yl)-pyrrole-2,5-dione was prepared from 6-isothiazol-5-yl-1-methyl-1H-indole and 2-(1-methyl-1H-indol-3-yl)-acetimidic acid isopropyl ester hydrochloride.

o) 3-[6-(1H-Imidazol-2-yl)-1-methyl-1H-indol-3-yl]-4-(1-methyl-6-nitro-1H-indol-3-yl)-pyrrole-2,5-dione was prepared from 1-methyl-6-[1-(2-trimethylsilanyl-ethoxymethyl)-1H-imidazol-2-yl]-1H-indole and 2-(1-methyl-6-nitro-1H-indol-3-yl)-acetimidic acid isopropyl ester hydrochloride followed by deprotection using aqueous hydrochloric acid in ethanol.

Example 3

3-(1-Methyl-1H-indol-3-yl)-4-(1-methyl-6-thiophen-2-yl-1H-indol-3-yl)pyrrole-2,5 dione To a solution of 3-(6-bromo-1-methyl-1H-indol-3-yl)-4-(1-methyl-1H-indol-3-yl)-pyrrole-2,5-dione as prepared in Example 2 (108 mg, 0.25 mmol) in dry THF(5 mL) was added tetrakis(triphenylphosphine)palladium (0) (6 mg, 0.005 mmol), 2-(tributylstalinyl) thiophenc (0.12 mL, 0.375 mmol) and triethylamine (0.10 mL, 0.70 mmol). The mixture was heated under reflux for 3 days and cooled to room temperature. Evaporation of the solvents and chromatography of the crude product over silica gel using 30% EtOAc in hexane gave 3-(1-methyl-1H-indol-3-yl)-4-(1-methyl-6-thiophen-2-yl-1H-indol-3-yl)-pyrrole-2,5-dione (72 mg, 66%).

Example 4

In a manner similar to that described in Example 3, the following compounds were prepared.

a) 3-(1-Methyl-1H-indol-3-yl)-4-(1-methyl-6-thiazol-2-yl-1H-indol-3-yl)pyrrole-2,5-dione (25 mg, 23%) was prepared from 3-(6-bromo-1-methyl-1H-indol-3-yl)-4-(1-methyl-1H-indol-3-yl)-pyrrole-2,5-dione (108 mg, 0.25 mmol) and 2-(tributylstannyl)thioazole (140 mg, 0.375 mmol).

b) 3-(1-Methyl-1H-indol-3-yl)-4-[1-methyl-6-(1-methyl-1H-imidazol-2-yl)-1H-indol-3-yl]-pyrrole-2,5-dione (46 mg, 38%) was prepared from 3-(6-bromo-1-methyl-1H-indol-3-yl)-4-(1-methyl-1H-indol-3-yl)pyrrole-2,5-dione (120 mg, 0.28 mmol) and 1-methyl-2-(tributylstannyl)imidazole (0.8 mL, containing 50% 1-methyl-imidazole) (Molloy, K. C.; Waterfield, P. C.; Mahon, M. F. *J. Organonetallic. Chem.* 1989, 365, 61.)

c) 3-(1-Methyl-6-nitro-1H-indol-3-yl)-4-(1-methyl-6-thiazol-2-yl-1H-indol-3-yl)pyrrole-2,5-dione (21 rng, 23%) was prepared from 3-(6-iodo-1-methyl-1H-indol-3-yl)-4-(1-methyl-6-nitro-1H-indol-3-yl)-pyrrole-2,5-dione (100 mg, 0.19 mmol) and 2-(tributylstannyl)thioazole (0.107 mL).

d) 3-(1-Methyl-6-nitro-1H-indol-3-yl)-4-(1-methyl-6-thiophen-2-yl-1H-indol-3yl)-pyrrole-2,5-dione (180 mg, 37%) was prepared from 3-(6-iodo-1-methyl-1H-indol-3-yl)-4-(1-methyl-6-nitro-1H-indol-3-yl)pyrrole-2,5-dione (525 mg, 1 mmol) and 2-(tributylstannyl)thiophene (0.98 mL, 3.09 mmol).

Example 5

3-(1-Methyl-1H-indol-3-yl)-4-(1-methyl-6-thiophen-3-yl-1H-indol-3-yl)pyrrole-2,5-dione Argon was bubbled through a solution of 3-(6-bromo-1-methyl-1H-indol-3-yl)-4-(1-methyl-1H-indol-3-yl)pyrrole-2,5-dione (160 mg, 0.37 mmol) in dioxane (15 mL) for 10 min. Tetrakis(triphenylphosphine)palladium (0) (8.5 mg, 0.007 mmol) and thiophene-3-boronic acid (52 mg, 0.41 mmol) and aqueous $Na_2CO_3$ (0.37 mL, 2M) were added. The mixture was refluxed for 2 h and more tetrakis (triphenylphosphine)palladium (0) (20 mg, 0.01 mmol) was added. Refluxing was continued for 24 h. The mixture was cooled and evaporated. Chromatography of the residue over silica using 50% EtOAc in hexane gave 3-(1-methyl-1H-indol-3-yl)-4-(1-methyl-6-thiophen-3-yl-1H-indol-3-yl) pyrrole-2,5-dione (117 mg, 72%).

Example 6

In a manner similar to that described in Example 5, 3-(1-methyl-6-nitro-1H-indol-3-yl)-4-(1-methyl-6-thiophen- 3-yl-1H-indol-3-yl)pyrrole-2,5-dione (11 mg, 12%) was prepared from 3-(6-iodo-1-methyl-1H-indol-3-yl)-4-(1-methyl-6-nitro-1H-indol-3-yl)-pyrrole-2,5-dione (100 mg, 0.19 mmol) and thiophene-3-boronic acid (49 mg, 0.38 mmol).

Example 7

3-(6-Imidazol-1-yl-1-methyl-1H-indol-3-yl)-4-(1-methyl-I H-indol-3-yl)pyrrole-2,5-dione a) An oven-dried re-sealable Schlenk tube was flushed with argon and charged with copper(I) trifluoromethane-sulfonate benzene complex (1.39 g, 2.76 mmol), 1.10-phenanthroline (5.69 g, 31.6 mmol), dibenzylideneacetone (740 mg, 3.16 mmol) and cesium carbonate (10 g, 30.7 mmol). Imidazole (3.23 g 44.8 mmol), 6-iodo-1-methyl-1H-indole (8.13 g, 31.6 mmol) and xylene (16 mL) were added and the tube was purged with argon. The tube was sealed and heated with stirring at 160° C. for 18 h. The mixture was cooled to room temperature and partitioned between $CH_2Cl_2$ (35 mL) and saturated aqueous $NH_4Cl$ (5 mL). The organic layer was separated and washed with brine. Then the organic extract was dried over $MgSO_4$, filtered and concentrated. The crude concentrate was filtered though a pad of silica gel and evaporated. Purification by HPLC afforded 6-imidazol-1-yl-1-methyl-1H-indole as a brown oil (3.1 g, 50%). [Ref: Kiyoori, A.; Marcoux, J-F.; Buchwald, S. L. *Tetrahedron Lett.*, 1999, 40, 2657.]

b) 6-Imidazol-1-yl-1-methyl-1H-indole (7.0 g, 35.5 mmol) was dissolved in $CH_2Cl_2$ (100 mL) (dried under 3A molecular sieves) at 0° C. A solution of oxalyl chloride in $CH_2Cl_2$ (2 M, 35.5 mL, 71 mmol) was added dropwise over 10 min. The mixture was stirred at 0° C. for 1.5 h and evaporated. Ether (100 mL) was added to the solid residue and after the mixture was stirred for 30 min, the resulting yellow solid was filtered off, washed with ether and dried under vacuum for 30 min. 1-Methyl-3-indoleacetimidic acid isopropyl ester hydrochloride (9.6 g, 36 mmol) and $CH_2Cl_2$ (200 mL) were added to the yellow solid at 0° C. $Et_3N$ (dried over 3A° molecular sieves) (30 mL) was added dropwise over 10 min. The orange-red mixture was stirred at room temperature overnight. The mixture was diluted with $CH_2Cl_2$ (300 mL) and washed with aqueous $Na_2CO_3$ (2×200 mL). The aqueous layer was back extracted with $CH_2Cl_2$ (100 mL). The combined organic extracts were washed with brine, dried ($K_2CO_3$) and evaporated. MeOH (100 mL) and concentrated HCl (37%, 10 mL) were added and the mixture was heated at reflux for 2 h. The reaction mixture was cooled, diluted with water (200 mL) and EtOAc (200 mL). The mixture was made basic using solid $K_2CO_3$ and extracted with EtOAc (4×200 mL). The combined organic extracts were washed with aqueous $Na_2CO_3$ (2×200 mL)

brine and dried ($K_2CO_3$). The mixture was passed through a pad of silica gel (10×10 cm) and the pad was washed with 10% methanol in EtOAc. Evaporation of the combined eluates gave the crude product as an orange solid. Recrystallization of the crude product using EtOAc, MeOH and $CHCl_3$ gave 3-(6-imidazol-1-yl-1-methyl-1H-indol-3-yl)-4-(1-methyl-1H-indol-3-yl)-pyrrole-2,5-dione (5.0 g, 33%) as an orange solid.

Example 8

In a manner similar to that described in example 7, the following compounds were prepared. The starting materials were prepared in a manner analogous to that described in example 7 a) 3-(6-Imidazol-1-yl-1-methyl-1H-indol-3-yl)-4-(1-methyl-6-nitro-1H-indol-3-yl)-pyrrole-2,5-dione (5.60 g, 64%) was prepared from 6-imidazol-1-yl-1-methyl-1H-indole (3.70 g, 18.7 mmol) and 2-(1-methyl-6-nitro-1H-indol-3-yl)acetimidic acid isopropyl ester hydrochloride (5.80 g, 18.7 mmol).

b) 3-[1-Methyl-6-(2-methyl-imidazol-1-yl)-1H-indol-3-yl]-4-(1-methyl-6-nitro-1H-indol-3-yl)-pyrrole-2,5-dione (23 mg, 5.5%) was prepared from 2-(1-methyl-6-(2-methyl-imidazol-1-yl)-1H-indole (260 mg, 0.87 mmol) and 2-(1-methyl-6-nitro-1H-indol-3-yl)acetimidic acid isopropyl ester hydrochloride (271 mg, 0.87 mmol).

c) 3-(1-Methyl-6-nitro-1H-indol-3-yl)-4-(1-methyl-6-pyrazol-1-yl-1H-indol-3-yl)pyrrole-2,5-dione was prepared from 1-methyl-6-pyrazol-1-yl-1H-indole and 2-(1-methyl-6-nitro-1H-indol-3-yl)acetimidic acid isopropyl ester hydrochloride.

d) 3(1-Methyl-1H-indol-3-yl)-4-(1-methyl-6-pyrazol-1-yl-1H-indol-3-yl)pyrrole-2,5-dione was prepared from 1-methyl-6-pyrazol-1-yl-1H-indole and 2-(1-methyl-1H-indol-3-yl)acetimidic acid isopropyl ester hydrochloride.

e) 3-(6-Bromo-1-methyl-1H-indol-3-yl)-4-(1-methyl-6-pyrazol-1-yl-1H-indol-3-yl)pyrrole-2,5-dione was prepared from 1-methyl-6-pyrazol-1-yl-1H-indole and 2-(6-bromo-1-methyl-1H-indol-3-yl)acetimidic acid isopropyl ester hydrochloride.

Example 9

3-(6-Imidazol-1-yl-1-methyl-1H-indol-3-yl)-4-(6-methoxy-1-methyl-1H-indol-3-yl)-pyrrole-2,5-dione a) 6-Imidazol-1-yl-1-methyl-1H-indole (0.90 g, 4.56 mmol) was dissolved in $CH_2Cl_2$ (2 mL) and cooled at 0° C. Methyl chlorooxoacetate (1.3 mL, 14 mmol) was added. Stirring was continued for 2 h at 0° C. and more methyl chlorooxoacetate (0.4 mL, 4.3 mmol) was added. After an additional 2 h, the solvent was removed. The residual solid was taken up in ether, filtered and washed well with ether to give crude methyl (6-imidazol-1-yl-1-methyl-1H-indol-3-yl)glyoxylate (1.50 g).

b) Crude methyl (6-imidazol-1-yl-1-methyl-1H-indol-3-yl)glyoxylate (1.40 g) in dioxane (100 mL) in a 250 mL round bottom flask was fitted with a reflux condenser and a balloon on the top. The system was flushed with argon then Pd/C (140 mg, 10%) was added, followed by sodium hypophosphite hydrate (7.2 g) in water (10 mL) and the mixture was heated under reflux overnight. More sodium hypophosphite hydrate (3.0 g) in water (5 ml,) and Pd/C (50 mg) were added. The mixture was refluxed for an additional 5 h, and cooled. The solvents were evaporated and the residue was diluted with EtOAc (100 mL). The solution was carefully washed with aqueous $NaHCO_3$ (2×100 mL). The combined aqueous layers were back extracted with EtOAc (2×200 mL). The combined organic extracts were filtered through a pad of silica gel and a layer of $MgSO_4$ on the top and the pad was washed with 10% methanol in $CH_2Cl_2$. The combined filtrate were evaporated and chromatography of the residue over silica gel using 1–6 % methanol in $CH_2Cl_2$ gave (6-imidazol-1-yl-1-methyl-1H-indolyl-3-yl)acetic acid methyl ester (230 mg, 17%).

c) (6-Imidazol-1-yl-1-methyl-1H-indol-3-yl)acetic acid methyl ester (230 mg, 0.85 mmol) was suspended in concentrated $NH_4OH$ (5 mL) in a 100 mL flask and stirred in a sealed flask for 24 h. Lyophilization of the mixture gave a crude product, which was chliomatographed on silica gel using 2–8% MeOH in $CH_2Cl_2$ to give (6-imidazol-1-yl-1-methyl-1H-indol-3-yl)acetamide (145 mg, 67%).

d) 6-Methoxy-1-methyl-1H-indole (1.0 g, 6.19 mmol) was dissolved in ether (10 mL) and cooled to 0° C. Methyl chlorooxoacetate (1.17 mL, 12.4 mmol) was added dropwise. Stirring was continued at 0° C. for 6 h. The mixture was filtered and washed well with ether to give methyl (6-methoxy-1-methyl-1H-indol-3-yl)glyoxylate (621 mg, 41%).

f) A solution of t-BuOK in THF (1 M, 0.53 mL, 0.53 mmol) was added dropwise to a mixture of methyl (6-methoxy-1-methyl-1H-indolyl-3)glyoxylate (47 mg, 0.18 mmol) and (6-imidazol-1-yl-1-methyl-1H-indol-3-yl)acetamide (46 mg, 0.1 8 mmol) at 0° C. The cooling bath was removed after 15 min and the mixture was stirred at room temperature for 3 h. Concentrated hydrochloric acid (1 mL) was added and the mixture was stirred for 30 min. Then the mixture was made basic with aqueous $NaHCO_3$ and extracted with EtOAc (3×50 mL). The combined organic extracts were washed with aqueous $NaHCO_3$ and dried ($K_2CO_3$). The extracts were filtered through a pad of silica gel and the pad was washed with 5% MeOH in EtOAc. Evaporation of the solvents and chromatography of the residue over silica gel using 70% EtOAc in hexanes and then EtOAc gave 32 mg of an orange solid which was then dissolved in 1:1 MeOH/$CH_2Cl_2$ (1 mL) and diluted with ether (8 mL). The resulting precipitate was filtered and washed with 1:1 ether/hexane (8 mL) to give 3-(6-imidazol-1-yl-1-methyl-1H-indol-3-yl)-4-(6-methoxy-1-methyl-1H-indol-3-yl)pyrrole-2,5-dione (29 mg, 36%). (RO 28-4240) Faul, M. M.; Winneroski, L. L.; Krumrich, C. A. *J. Org. Chem.* 1998, 63, 6053.

Example 10

In a manner similar to that described in Example 9 the following compounds were prepared. The starting materials were prepared in a manner analogous to that described in 9(c) and (d).

a) 3-(6-Bromo-1-methyl-1H-indol-3-yl)-4-(6-imidazol-1-yl-1-methyl-1H-indol-3-yl)-pyrrole-2,5-dione (13 mg, 19%): prepared from methyl (6-bromo-1-methyl-1H-indol-3)glyoxylate (43 mg, 0.14 mmol) and (6-imidazol-1-yl-1-methyl-1H-indol-3-yl)acetamide (50 mg, 0.20 mmol).

b) 3-[4-(6-Imidazol-1-yl-1-methyl-1H-indol-3-yl)-2,5-dioxo-2,5-dihydro-1H-pyrrole-3-yl]-1-methyl-1H-indole-6-carbonitrile (14 mg, 16%): prepared from methyl (6-cyano-1-methyl-1H-indol-3)glyoxylate (44 mg, 0.18 mmol) and (6-imidazol-1 -yl-1-methyl-1H-indol-3-yl)-acetamide (46 mg, 0.18 mmol).

Example 11

3-(1-Methyl-1H-indol-3-yl)-4-(1-methyl-6-morpholin-4-yl-1H-indol-3-yl)pyrrole 2,5-dione a) An oven dried flask was flushed with argon and charged with 18-crown-6 (15 g, 56.7 mmol), 6-iodo-1-methyl-1H- indole (10.4 g, 40.46 mmol), morpholine (4.3 mL, 48.6 mmol), sodium t-butoxide (5.42 g, 54.7 mmol), tris (dibenzylidene acetone)dipalladium (0) (186 mg, 0.20 mmol) and 2,2'-bis(diphenylphosphino)-1,1-binaphthyl) (380 mg, 0.61 mmol). The flask was flushed with argon for 10 min and dry THF (80 mL) was added. The mixture was stilled at room temperature for 5 h, then diluted with ether and washed with brine. The organic layer was dried (MgSO$_4$), evaporated and the crude product was purified by chromatography on silica gel using 5–30% ether/hexanes to give 1-methyl-6-morpholin-4-yl-1H-indole (8.17 g, 94%). [Ref: Wolfe, J. P.; Buchwald, S. L. *J. Org. Chem.* 1997, 62, 6066.]

6-Iodo-1-methyl-1H-indole was prepared in a similar manner as described in example 1(a).

b) A solution of 1-methyl-6-morpholin-4-yl-1H-indole (0.50 g, 2.31 mmol) in CH$_2$Cl$_2$ (5 mL) (dried over 3A° molecular sieves) was cooled to 0° C. Oxalyl chloride (0.4 mL, 4.62 mmol), was added dropwise over 5 min. The mixture was stirred at 0° C. for 4 h and evaporated. The residual solid was triturated with ether, filtered, washed with ether and dried under vacuum for 30 min. 1-Methyl -3-indoleacetimidic acid isopropyl ester hydrochloride (0.58 g, 2.20 mmol) and CH$_2$Cl$_2$ (9 mL) were added to the yellow solid at 0° C. Et$_3$N (dried over 3A° molecular sieve) (1.8 mL) was added dropwise over 10 min. and then the orange-red mixture was stirred at room temperature overnight. The mixture was diluted with EtOAc, washed with 1 N NaOH and the aqueous layer was back-extracted with EtOAc. The combined organic extracts were washed with brine, dried (K$_2$CO$_3$) and evaporated. The residue was dissolved in MeOH (100 mL) containing TsOH.H$_2$O (3.30 g, 17.3 mmol ) and the mixture was stirred at room temperature for 4 h. After the solvents were removed under reduced pressure the residue was diluted with EtOAc (500 mL) and made basic using aqueous NaHCO$_3$. The organic layer was separated and the aqueous layer was back extracted with EtOAc. The combined organic extracts were washed with brine, dried (MgSO$_4$), and evaporated. Chromatography of the residue over silica gel using 30–70% EtOAc/hexanes gave 3-(1-methyl-1H-indol-3-yl)-4-(1-methyl-6-morpholin-4-yl-1H-indol-3-yl)pyrrole 2,5-dione (0.30 g, 30%) as an orange solid.

Example 12

In a manner similar to that described in Example I the following compounds were prepared. The starting materials were prepared in a manner analogous to that described in 11(a).

a) 3-(1-Methyl-6-morpholin-4-yl-1H-indol-3-yl)-4-(1-methyl-6-nitro-1H-indol-3-yl)pyrrole-2,5-dione (315 mg, 25%): prepared from 1-methyl-6-morpholine-4-yl-1H-indole (0.56 g, 2.56 mmol) and 2-(1-methyl-6-nitro-1H-indol-3-yl)acetimidic acid isopropyl ester hydrochloride (0.81 g, 2.56 mmol).

b) 3(1,6-Dimethyl-1H-indol-3-yl)-4-(1-methyl-6-morpholin-4-yl-1H-indol-3-yl)pyrrole-2,5-dione: prepared from 1,6-dimethyl-1H-indole and 2-(1-methyl-6-morpholin-4-yl-1H-indol-3-yl)-acetimidic acid isopropyl ester hydrochloride.

c) 3-(1H-Indol-3-yl)-4-(1-methyl-6-morpholin-4-yl-1H-indol-3-yl)pyrrole-2,5-dione: prepared from 1-methyl-6-morpholin-4-yl-1H-indole and 2-[1-(2,2-dimethyl-propionyl)-1H-indol-3-yl]acetimidic acid isopropyl ester hydrochloride followed by deprotection using sodium methoxide in methanol.

d) 3-(1-Methyl-6-nitro-1H-indol-3-yl)-4-(1-methyl-6-pyrrolidin-1-yl-1H-indol-3-yl)pyrrole-2,5-dione (0.96 g, 28%): prepared as a dark brown solid using 1-methyl-6-pyrrolidin-1-yl-1H-indole (1.60 g, 8 mmol), and 2-(1-methyl-6-nitro-1H-indol-3-yl)acetimidic acid isopropyl ester hydrochloride (2.24 g, 7.2 mmol).

e) 3-(6-Fluoro- 1-methyl-1H-indol-3-yl)-4-(6-pyrrolidin-1-yl-1H-indol-3-yl)pyrrole-2,5-dione was prepared from 6-pyrrolidin-1-yl-1H-indole and 2-(6-fluoro-1 -methyl-1H-indol-3-yl)-acetimidic acid isopropyl ester hydrochloride.

6-Pyrrolidin-1-yl-1H-indole was prepared as follows:

a) A mixture of 1-methyl-6-nitro-1H-indole (5.0 g, 28.4 mmol) and 10% Pd/C(1.0 g) in ethanol (200 ml) and tetrahydrofuran (100 ml) was hydrogenated at atmospheric pressure for 14 hours. The reaction mixture was filtered and concentrated to give 1-methyl-6-amino-1H-indole after crystallization from ether/hexane (3.8 g, 80%).

b) A mixture of 1-methyl-6-amino-1H-indole (11 g, 83 mmol) and succinic anhydride (8.3 g, 83 mmol) in toluene (150 ml) was heated to reflux for 1 hour. The reaction mixture was cooled and evaporated to give a solid (18.0). A mixture of resulting solid (10.1 g) and sodium acetate (3.45 g, 42 mmol) in acetic anhydride (36 mL) was heated at reflux for 15 minutes. The reaction mixture ws cooled to room temperature and ice-water was added slowly to it. The mixture was stirred for 15 minutes and extracted with ethyl acetate-tetrahydrofuran. The combined organic extracts were washed with brine and dried over magnesium sulfate. Evaporation of the solvent gave a crude product, which was further purified by recrystallizing in ethyl acetate-hexanes to give (1-methyl-1H-indol-6-yl)-pyrrolidine-2,5-dione (6.0 g).

c) 1-(1-Methyl-1H-indol-6-yl)-pyrrolidine-2,5-dione (3.8 g, 17.7 mmol) in tetrahydrofuran (75 ml) was treated with lithium aluminum hydride in tetrahydrofuran (88 ml, 1.0 M, 88 mmol) for 2 hours at room temperature. The mixture was cooled and treated with aqueous sodium sulfate. The mixture was extracted with ether and the organic layer was concentrated. Chromatography of the crude product over silica gel with 70% hexane/ethyl acetate gave 6-pyrrolidin-1-yl-1H-indole as a white solid.

f) 3-(6-Chloro-1-methyl-1H-indol-3-yl)-4-(6-pyrrolidin-1-yl-1H-indol-3-yl)pyrrole-2,5-dione (1.2%) was prepared from 6-pyrrolidin-1-yl-1H-indole and 2-(6-chloro-1-methyl-1H-indol-3-yl)acetimidic acid isopropyl ester hydrochloride.

g) 3-(1-Methoxymethyl-6-pyrrolidin-1-yl-1H-indol-3-yl)-4-(1-methyl-6-nitro-1H-indol-3-yl)pyrrole-2,5-dione was prepared from 1-methoxymethyl-6-pyrrolidin-1-yl-1H-indole and 2-(1-methyl-6-nitro-1H-indol-3-yl)acetimidic acid isopropyl ester hydrochloride.

1-Methoxymethyl-6-pyrrolidin-1-yl-1H-indole was prepared from 6-pyrrolidin-1-yl-1H-indole ( example 12 e) in the same manner as example 1(a) using chloromethyl methylether as the alkylating agent.

h) 3-(1-Methyl-6-nitro-1H-indol-3-yl)-4-(6-pyrrolidin-1-yl-1H-indol-3-yl)pyrrole-2,5-dione: prepared by refluxing 3-(1-methoxymethyl-6-pyrrolidin-1-yl-1H-indol-3-yl)-4-(1-methyl-6-nitro-1H-indol-3-yl)-pyrrole-2,5-dione (above) in a mixture of acetic acid and aqueous HCl. After an aqueous work-up, the crude product was purified by silica gel chromatography.

i) 3-(1H-indol-3-yl)-4-(1-methyl-6-pyrrolidin-1-yl-1H-indol-3-yl)-pyrrole-2,5-dione: prepared using 1-methyl-6-pyrrolidin-1-yl-1H-indole and 2-[1-(2,2- dimethylpropionyl)-1H-indol-3-yl]acetimidic acid isopropyl ester hydrochloride followed by deprotection using sodium methoxide in methanol.

j) 3-(1-Methyl-1H-indol-3-yl)-4-(1-methyl-6-pyrrolidin-1-yl-1H-indol-3-yl)pyrrole-2,5-dione (41 mg, 13%) was prepared using 1-methyl-6-pyrrolidin-1-yl-1H-indole (150 mg, 0.75 mmol) and 1-methyl-3-indoleacetimidic acid isopropyl ester hydrochloride (200 mg, 0.75 mmol).

k) 3-(1-Methyl-1H-indol-3-yl)-4-[1-methyl-6-(4-methyl-piperazin-1-yl)-1H-indol-3-yl]pyrrole-2,5-dione (256 mg, 67%): prepared from 1-methyl-6-(4-methylpiperazin-1-yl)-1H-indole (192 mg, 0.84 mmol), prepared as described in Example 11(a), and 1-methyl-3-indoleacetimidic acid isopropyl ester hydrochloride (224 mg, 0.84 mmol).

l) 3-(1-Methyl-1H-indol-3-yl)-4-(1-methyl-6-piperidin-1-yl-1H-indol-3-yl)pyrrole-2,5-dione (56 mg, 28%): prepared from 1-methyl-6-piperidin-1-yl-1H-indole (96 mg, 0.45 mmol) and 1-methyl-3-indoleacetimidic acid isopropyl ester hydrochloride (120 mg, 0.45 mmol).

m) 3-(6-Fluoro-1-methyl-1H-indol-3-yl)-4-(1-methoxymethyl-6-morpholin-4-yl-1H-indol-3-yl)pyrrole-2,5-dione: prepared from 1-methoxymethyl-6-morpholin-4-yl-1H-indole and 2-(6-fluoro-1-methyl-1H-indol-3-yl) acetimidic acid isopropyl ester hydrochloride.

n) 3-(6-Fluoro-1-methyl-1H-indol-3-yl)-4-(6-morpholin-4-yl-1H-indol-3-yl)-pyrrole-2,5-dione: prepared from 3-(6-fluoro-1-methyl-1H-indol-3-yl)-4-(1-methoxymethyl-6-morpholin-4-yl-1H-indol-3-yl)pyrrole-2,5-dione by deprotection using hydrochloric acid in refluxing THF followed by refluxing in aqueous acetic acid.

o) 3-(1-Methyl-1H-indol-3-yl)-4-(6-morpholin-4-yl-1H-indol-3-yl)pyrrole-2,5-dione: prepared from 1-(4-methoxybenzyl)-6-morpholin-4-yl-1H-indole and 1-methyl-3-indoleacetimidic acid isopropyl ester hydrochloride followed by deprotection using sulfuric acid in trifluoroacetic acid.

Example 13

1-Methyl-3-[4-(1-methyl-6-morpholin-4-yl-1H-indol-3-yl)-2,5-dioxo-2,5-dihydro-1H-pyrrole-3-yl]-1H-indole-6-carbonitrile a) 1-Methyl-6-morpholin-4-yl-1H-indole (3.89 g, 18 mmol) was dissolved in $CH_2Cl_2$ (18 mL) and cooled at 0° C. Methyl chlorooxoacetate (2.4 mL, 26 mmol) was added to give a dark solution. Stirring was continued for 2 h at 0° C. and more methyl chlorooxoacetate (0.40 mL, 4.3 mmol) was added. After a further 2 h, the solvent was evaporated. The resulting solid was taken up in ether, filtered and washed well with ether to give crude methyl (1-methyl-6-morpholin-4-yl-1H-indol-3-yl)glyoxylate (6 g).

b) Crude methyl (1-methyl-6-morpholin-4-yl-1H-indolyl-3)glyoxylate (6 g) in dioxane (300 mL) in a 500 mL round bottom flask was fitted with a reflux condenser and a balloon on the top. The system was flushed with argon then Pd/C (2 g, 10%) was added followed by sodium hypophosphite hydrate (20 g) in water (50 mL). The mixture was heated under reflux for 5 h and more sodium hypophosphite hydrate (10 g) in water (10 mL) was added. The mixture was refluxed for additional 3 h. and cooled. The solids were filtered off and washed well with EtOAc. The filtrate was washed with brine and dried ($MgSO_4$). Evaporation of the solvents and chromatography of the residue over silica gel using 20% EtOAc in hexanes gave (1-methyl-6-morpholin-4-yl-1H-indol-3-yl)acetic acid methyl ester (2.79 g, 54%).

c) (1-Methyl-6-morpholin-4-yl-1H-indol-3-yl)-acetic acid methyl ester (2.67 g, 9.26 mmol) was suspended in concentrated $NH_4OH$ (20 mL) in a 100 mL flask, sealed and stirred for 24 h. The mixture was transferred into a 500 mL flask and more $NH_4OH$ (80 mL) was added. The flask was again sealed and stirring was continued for another 24 h. The volatiles were removed under reduced pressure. (1-methyl-6-morpholin-4-yl-1H-indol-3-yl)acetamide (2.39 g, 94%) was obtained after lyophilization.

d) A solution of t-BuOK in THF (1 M, 18.9 mL, 18.9 mmol) was added dropwise to a mixture of methyl (6-cyano-1-methyl-1H-indol-3-yl)glyoxylate (1.85 g, 7.64 mmol) and (1-methyl-6-morpholin-4-yl-1H-indol-3-yl)-acetamide (1.74 g, 6.36 mmol) at 0° C. The cooling bath was removed after 15 min and the mixture was stirred at room temperature for 3 h. Concentrated hydrochloric acid (37%, 10 mL) was added and the reaction mixture was stirred for a further 30 min. The mixture was made basic with aqueous $NaHCO_3$ and extracted with $CHCl_3$ (3×500 mL). The combined organic extracts were washed with aqueous $Na_2CO_3$ and dried ($K_2CO_3$). The extracts were filtered through a pad of silica gel, then evaporation of the solvents and crystallization of the crude product from acetone/EtOAc gave 1-methyl-3-[4-(1-methyl-6-morpholin-4-yl-1H-indol-3-yl)-2,5 -dioxo-2,5-dihydro-1H-pyrrole-3-yl-]-1H-indole-6-carbonitrile (2.05 g, 69%). Ref: Faul, M. M.; Winneroski, L. L.; Krumrich, C. A. *J. Org. (Chem.* 1998, 63, 6053.

Example 14

In a manner similar to that described in Example 13, the following compounds were prepared. The starting materials were prepared in a manner analogous to that described in 13a), b), and c).

a) 3-(6-Methoxy-1-methyl-1H-indol-3-yl)-4-(1-methyl-6-morpholin-4-yl-1H-indol-3-yl)pyrrole-2,5-dione (103 mg, 23%): prepared from methyl (6-methoxy-1-methyl-1H-indol-3-yl)glyoxylate (257 mg, 1.04 mmol) and (1-methyl-6-morpholin-4-yl-1H-indol-3-yl)acetamide (259 mg, 0.95 mmol).

b) 3-(6-Fluoro-1-methyl-1H-indol-3-yl)-4-(1-methyl-6-morpholin-4-yl-1H-indol-3-yl)pyrrole-2,5-dione (72 mg, 42%): prepared from methyl (6-fluoro-1-methyl-1H-indol-3-yl)glyoxylate (95 mg, 0.40 mmol) and (1-methyl-6-morpholin-4-yl-1H-indol-3-yl)acetamide (100 mg, 0.37 mmol).

c) 3-(6-Chloro-1-methyl-1H-indol-3-yl)-4-(1-methyl-6-morpholin-4-yl-1H-indol-3-yl)pyrrole-2,5-dione (96 mg, 83%): prepared from methyl(6-chloro-1-methyl-4-1H-indol-3-yl)glyoxylate (74 mg, 0.29 mmol) and (1-methyl-6-morpholin-4-yl-1H-indol-3-yl)-acetamide (67 mg, 0.245 mmol).

d) 3-(6-Bromo-1-methyl-1H-indol-3-yl)-4-(1-methyl-6-morpholin-4-yl-1H-indol-3-yl)pyrrole-2,5-dione (139 mg, 49%) was prepared from methyl (6-bromo-1-methyl-1H-indol-3-yl)glyoxylate (190 mg, 0.64 mmol) and (1-methyl-6-morpholin-4-yl-1H-indol-3-yl)acetamide (150 mg, 0.55 mmol).

e) 3-(1-Methyl-6-morpholin-4-yl-1H-indol-3-yl)-4-(1-methyl-6-trifluoromethyl-1H-indol-3-yl)pyrrole-2,5-dione (151 mg, 54%) was prepared from methyl (1-methyl-6-trifluromethyl-1H-indol-3-yl)glyoxylate (172 mg, 0.60 mmol) and (1-methyl-6-morpholin-4-yl-1H-indol-3-yl) acetamide (150 mg, 0.55 mmol).

f) 3-(6-Bromo-1-methyl-1H-indol-3-yl)-4-(1-methyl-6-pyrrolidin-1-yl-1H-indol-3-yl)pyrrole-2,5-dione (49 mg, 46%) was prepared from methyl (6-bromo-1-methyl-1H-indol-3-yl)-glyoxylate (68 mg, 0.23 mmol) and (1-methyl-6-pyrrolidin-4-yl-1H-indol-3-yl)acetamide (54 mg, 0.21 mmol).

g) 3-(6-Methoxy-1-methyl-1H-indol-3-yl)-4-(1-methyl-6-pyrrolidin-1-yl-1H-indol-3-yl)pyrrole-2,5-dione (55 mg, 58%) was prepared from methyl (6-methoxy-1methyl -1H-indol-3-yl)-glyoxylate (57mg, 0.23 mmol) and (1-methyl-6-pyrrolidin-1-yl-1H-indol-3-yl)-acetamide (54 mg, 0.21 mmol).

h) 3-(1-Methyl-6-pyrrolidin-1-yl-1H-indol-3-yl)-4-(1-methyl-6-trifuloromethyl-1H-indol-3-yl)pyrrole-2,5-dione (67 mg, 35%) was prepared from methyl (1-methyl-6-trifluoromethyl-1H-indol-3-yl)glyoxylate (111 mg, 0.39 mmol) and (1-methyl-6-pyrrolidin-1-yl-1H-indol-3-yl) acetamide (100 mg, 0.39 mmol).

i) 3-(6-Chloro-1-methyl-1H-indol-3-yl)-4-(1-methyl-6-pyrrolidin-1-yl-1H-indol-3-yl)pyrrole-2,5-dione (70 mg, 37%) was prepared from methyl (6-chloro-1-methyl-1H-indol-3-yl)glyoxylate (98 mg, 0.39 mmol) and (1-methyl-6-pyrrolidin-1-yl-1H-indol-3-yl)-acetamide (100 mg, 0.39 mmol).

Example 15

1-Methyl-3-[4-(1-methyl-6-pyrrolidin-1-yl-1H-indol-3-yl)-2,5-dioxo-2,5dihydro-1H-pyrrole-3-yl]-1H-indole-6-carbonitrile a) (1-Methyl-6-pyrrolidin-1-yl-1H-indol-3-yl)acetic acid methyl ester (360 mg, 1.32 mmol) and NaOH (132 mg, 3.3 mmol) in methanol (8 mL) were heated at reflux for 30 min. The reaction mixture was cooled to 0° C. and acidified using 1 N HCl. The mixture was extracted with EtOAc (3×100 mL) and $CH_2Cl_2$ (3×100 mL). The combined organic extracts were dried ($MgSO_4$) and concentrated. Chromatography of the crude product over silica gel using 5–20% MeOH in $CH_2Cl_2$ gave (1-methyl-6-pyrrolidin-1-yl-1H-indol-3-yl)acetic acid (241 mg, 71%).

(1-methyl-6-pyrrolidin-1-yl-1H-indol-3-yl)-acetic acid methyl ester was prepared in a similar maimer as described in examples 13 a) and b).

b) A solution of oxalyl chloride in $CH_2Cl_2$ (2 M, 1.6 mL, 3.2 mmol) was added dropwise to a solution of 6-cyano-1-methyl-1H-indole (360 mg, 2.3 mmol) in ether (5 mL). Stirring was continued for 30 min at 0° C. and the cooling bath was removed. After 2 h, more of the 2 M solution of oxalyl chloride (0.2 mL, 0.4 mmol.) was added. Stirring was continued at room temperature for additional 2 h. The solid was filtered and washed with ether to give (6-cyano-1-methyl-1H-indol-3-yl)glyoxylyl chloride (450 mg, 79%). Ref:: Troxler, F.; Hamisch, A.; Bormann, G.; Seemann, F.; Szabo, L.; *Helv. Chim Acta*, 1968, 51(1), 1616.

c) 6-Cyano-1-methyl-1H-indolyl-3-glyoxylyl chloride (260 mg, 1.05 mmol) and (1-methyl-6-pyrrolidin-1-yl-1H-indol-3-yl)-acetic acid (241 mg, 0.93 mmol) in $CH_2Cl_2$ (5 mL) were stirred at 0° C. Triethylamine (0.41 mL. 2.95 mmol) was added and the mixture was stirred at room temperature for 16 h. The solvent was removed under vacuum and toluene (10 mL) and p-TsOH.$H_2O$ (0.35 g, 1.84 mmol) were added to the residue. After 2 h, methanol (5 mL) was added and stirring was continued until the presence of starting material could not be detected by TLC (40% EtOAc/hexanes). The mixture was diluted with $CH_2Cl_2$ (50 mL) and washed with saturated $Na_2CO_3$ (3×50 mL). The aqueous layer was back extracted with $CH_2Cl_2$ (2×50 mL). The combined organic extracts were dried ($MgSO_4$) and evaporated to give 0.30 g of a purple solid. Chromatography of the crude product over silica gel using 5%–20% EtOAc/hexanes gave 1-methyl-3-[4-(1-methyl-6-pyrrolidin-1-yl-1H-indol-3-yl)-2,5-dioxo-2,5-dihydro-furan-3-yl]-1H-indole-6-carbonitrile (0.19 g, 45%) as a purple solid.

d) 1-Methyl-3-[4-(1-methyl-6-pyrrolidin-1-yl-1H-indol-3-yl)-2,5-dioxo-2,5-dihydro-furan-3-yl]-1H-indole-6-carbonitrile (0.16 g, 0.36 mmol) was dissolved in dry DMF (5 mL, dried over 3A° molecular sieves) in a 50 mL round bottom flask. To this was added methanol (0.1 mL) and 1,1,1,3,3,3 hexamethyldisilazane (0.9 mL). The purple solution was stirred at room temperature overnight. Methanol (0.03 mL) and 1,1,1,3,3,3 hexamethyldisilazane (0.27 mL) were added and stirred for 3 h. The mixture was diluted with ethyl acetate (50 mL) and washed with brine. The aqueous layer was back extracted with ethyl acetate (2×50 mL). The combined organic extracts were diluted with an equal volume of hexanes, dried ($MgSO_4$), and passed over a pad of silica gel. The silica gel was washed a with 1:1 ethyl acetate/hexanes (150 mL), and the filtrate was concentrated. Chromatography of the residue over silica gel using 25%–40% EtOAc/hexanes gave 1-methyl-3-[4-(1-methyl-6-pyrrolidin-1-yl-1H-indol-3-yl)-2,5-dioxo-2,5-dihydro-1H-pyrrole-3-yl]-1H-indole-6-carbonitrile (71 mg, 44%) as a purple solid.

Example 16

3-(6-methoxymethyl-1-methyl-1H-indol-3-yl)-4-(1-methyl-6-morpholin-4-yl-1H-indol-3-yl)pyrrole-2,5-dione: prepared from 6-methoxymethyl-1-methyl-1H-indole and 1-methyl-6-morpholin-4-yl-1H-indole Example 17

3-[6-(2-Imidazol-1-yl-ethoxy)-1-methyl-1H-indol-3-yl]-4-(1-methyl-6-nitro-1H-indol-3-yl)pyrrole-2,5-dione a) A solution of n-butyllithium in hexane (1.6 M, 1.7 mL, 27.2 mmol) was added to 6-bromo-1-methyl indole (5.0 g, 23.8 mmol) in dry THF (100 mL) at −78° C. over 30 min. After 30 min, trimethylborate (2.93 g, 28.2 mmol) in dry THF (25 mL) was added. Stirring was continued at −78° C. for 30 min. Methanol (12.5 mL) and water (12.5 mL) were added, and the mixture was stirred at room temperature for 3 h. It was diluted with ether (100 mL), and washed with sulfuric acid (1 N, 2×100 mL) and water (2×100 mL). The aqueous layer was back extracted with ether (2 ×100 mL). The combined organic extracts were dried ($MgSO_4$), filtered over a pad of silica gel and the pad was washed with ether (100 mL). The filtrate was concentrated and the crude product was chromatographed over silica gel with 10% to 25% ethyl acetate/hexanes to give 1-methyl-1H-indol-6-yl-boronic acid (2.6 g, 62.5%).

b) 1-Methyl-1H-indol-6-yl-boronic acid (1.4 g, 8.0 mmol) was dissolved in ether (25 mL). Hydrogen peroxide (15%, 6 mL) was added over 5 minutes and the reaction mixture was stirred at room temperature for 1 h. The mixture was extracted with NaOH (1N, 2×50 mL) and the aqueous extracts were washed with ether (2×50 mL). The aqueous layers were cooled to 0° C. and acidified to pH 4.0 with 6 N HCl. The mixture was extracted with ether (3×100 mL) and the organic extracts were washed with water. The organic extracts were dried ($MgSO_4$), filtered through a pad of silica gel and the pad was washed with ether (100 mL). After the filtrate was concentrated, the residue was chromatographed over silica gel with 10% to 20% ethyl acetate/hexanes to give 1-methyl-1H-indol-6-ol as a yellow solid (0.56 g, 47%).

c) 1-Methyl-1H-indol-6-ol (0.36 g, 2.45 mmol), 1-(2-hydroxyethyl)imidazole (0.315 g, 2.82 mmol) and triphenylphosphine (0.767 g, 2.92 mmol) were dissolved in dry THF under argon at −78° C. Diethyl azodicarboxylate (0.47 mL, 2.95 mmol) was added over 2 min. The mixture was stirred at room temperature for 16 h. More triphenyl phosphine (0.7 g, 2.67 mmol) and DEAD (0.47 mL, 2.95 mmol) were added at −78° C. The reaction mixture was stirred for 24 h at room temperature then was diluted with ether (50 mL) and washed with water (2×50 mL). The aqueous layer was back-extracted with ether (2×50 mL) and the combined organic extracts were dried (MgSO$_4$) and evaporated. The crude red-orange oil was passed over a pad of silica gel and the pad was washed with 10% methanol/methylene chloride (200 mL) to yield a maroon oil (3.15 g). Chromatography of the crude product over silica gel with 0–10% methanol/chloroform gave 6-(2-imidazol-1-yl-ethoxy)-1-methyl-1H-indole (0.19 g, 32%) as a thick brown oil.

d) 6-(2-Imidazol-1-yl-ethoxy)-1-methyl-1H-indole (185 mg, 0.77 mmol) was dissolved in CH$_2$Cl$_2$ (2 mL) under argon at 0° C. To this was added oxalyl chloride (0.19 mL, 2.18 mmol) in CH$_2$Cl$_2$ (2 mL). After stirring at 0° C. for 4 h, the mixture was evaporated and dried under vacuum for 2 h. 2-(1-Methyl-6-nitro-1H-indol-3-yl)acetimidic acid isopropyl ester hydrochloride (239 mg, 0.77 mmol) and CH$_2$Cl$_2$ (3mL) were added to the above green solid. Triethylamine (0.81 mL, 5.82 mmol) was added slowly at 0° C. and the mixture was stirred at room temperature for 16 h. The mixture was evaporated to dryness and methanol (5 mL) and 12 N hydrochloric acid (1 mL) were added. The mixture was heated to 85° C. for 1 h. After the solvents were evaporated, ethyl acetate (50 mL) was added and the mixture was carefully washed with 5% sodium bicarbonate (3×50 mL). The aqueous layer was back-extracted with ethyl acetate (2×50 mL), then the combined organic extracts were dried (MgSO$_4$), filtered though a pad of silica gel and the pad was washed with 10% methanol/CH$_2$C$_2$ (400 mL). The filtrates were concentrated and the crude product was chromatographed on silica gel with 1% to 5% methanol/ethyl acetate gave an orange solid. Further purification by dissolving the solid in hot CH$_2$C$_2$ (3 mL) and precipitating with ether (20 mL) yielded 3-[6-(2-imidazol-1-yl-ethoxy)-1-methyl-1H-indol-3-yl]-4-(1-methyl-6-nitro-1H-indol-3-yl)-pyrrole-2,5-dione as an orange solid (0.103 g, 26%).

Example 18

3-(1-Methyl-6-nitro-1H-indol-3-yl)-4-(1-methyl-6-pyrimidin-5-yl-1H-indol-3-yl)pyrrole-2,5-dione a) 1-methyl-1H-indol-6-yl-boronic acid (from example 17(b) (0.86 g, 5 mmol) was suspended in dry dioxaie (20 ml) and treated with 5-bromo-pyrimidine (1.0 g, 6.3 mmol), sodium carbonate (2.0 g), and tetrakis(triphenylphosphine)palldium (0) (120 mg, 0.10 mmol). The mixture was refluxed for 16 hr and cooled. This was diluted with hexane (20 ml), filtered through celite, and concentrated to dryness. The residue was purified by silica gel chromatography using ethyl acetate as solvent. 1-Methyl-6-pyrimidin-5-yl-1H-indole was crystallized from ether.

b) 3-(1-Methyl-6-nitro-1H-indol-3-yl)-4-(1-methyl-6-pyrimidin-5-yl-1H-indol-3-yl)pyrrole-2,5-dione was prepared from 1-methyl-6-pyrimidin-5-yl-1H-indole and 2-(1-methyl-6-nitro-1H-indol-3-yl)-acetimidic acid isopropyl ester hydrochloride.

Example 19

3-(1-Methyl-1-indol-3-yl)-4-(1-methyl-6-pyrimidin-5-yl-1H-indol-3-yl)pyrrole-2,5-dione: prepared from 1-methyl-6-pyrimidin-5-yl-1H-indole and 1-methyl-3-indole-acetimidic acid isopropyl ester hydrochloride as described in Example 18

Example 20

| | | CAPSULE FORMULATION | | | | |
|---|---|---|---|---|---|---|
| | | mg/Capsule | | | | |
| Item | Ingredients | 10 mg | 50 mg | 100 mg | 250 mg | 500 mg |
| 1 | Example 12d | 10.0 | 50.0 | 100.0 | 250.0 | 500.0 |
| 2 | Hydrous Lactose | 154.0 | 114.0 | 148.0 | 42.0 | 82.0 |
| 3 | Starch 1500 | 25.0 | 25.0 | 40.0 | 40.0 | 70.0 |
| 4 | Talc | 10.0 | 10.0 | 10.0 | 15.0 | 20.0 |
| 5 | Magnesium Stearate | 1.0 | 1.0 | 2.0 | 3.0 | 3.0 |
| | Total Fill Weight | 200 | 200 | 300 | 350 | 675 |

Manufacturing Procedure:

1. Mix Items 1, 2 and 3 in a suitable mixer for 15 minutes.
2. Pass the mix from Step 1 through a Fitz mill using "00" screen at slow speed.
3. Add the adjusted amount of Items 4 and 5 and mix for 3 minutes in a suitable mixer.
4. Fill the powder mix from Step 3 into a suitable size capsules.

Example 21

| | | TABLET FORMULATION | | | | | |
|---|---|---|---|---|---|---|---|
| | | mg/Tablet | | | | | |
| Item | Ingredients | 10 mg | 50 mg | 100 mg | 400 mg | 600 mg | 1000 mg |
| KERNEL | | | | | | | |
| 1 | Example 12d | 10.0 | 50.0 | 100.0 | 400.0 | 600.0 | 1000.0 |
| 2 | Anhydrous Lactose | 177.0 | 137.0 | 84.5 | 279.5 | 79.5 | 102.0 |
| 3 | Croscarmellose Sodium | 5.0 | 5.0 | 7.5 | 40.0 | 40.0 | 50.0 |
| 4 | Povidone K 30 | 6.0 | 6.0 | 6.0 | 23.0 | 23.0 | 36.0 |
| 5 | Magnesium Stearate | 2.0 | 2.0 | 2.0 | 7.5 | 7.5 | 12.0 |
| | Kernel Weight | 200 | 200 | 200 | 750 | 750 | 1200 |

-continued

TABLET FORMULATION

| | | mg/Tablet | | | | | |
|---|---|---|---|---|---|---|---|
| Item | Ingredients | 10 mg | 50 mg | 100 mg | 400 mg | 600 mg | 1000 mg |
| FILM COAT | | | | | | | |
| 6 | Hydroxypropyl Methylcellulose 6cps-2910 | 3.0 | 3.0 | 3.0 | 6.0 | 9.0 | 12.0 |
| 7 | Talc | 1.5 | 1.5 | 1.5 | 3.0 | 4.5 | 6.0 |
| 8 | Titanium Dioxide | 1.5 | 1.5 | 1.5 | 3.0 | 4.5 | 6.0 |
| Total tablet weight | | 206 | 206 | 206 | 759 | 768 | 24.0 |

Manufacturing Procedure:

1. Mix Items 1, 2, 3 and 4 in a high shear mixer for 5 minutes.
2. Granulate the powder mix from Step 1 with purified water.
3. Dry the granulation from Step 2 at 50° C.
4. Pass the granulation from Step 3 through a suitable milling equipment.
5. Add the adjusted amount of Item 5 to the milled granulation from Step 4 and mix for 5 minutes in a suitable mixer.
6. Compress the granulation from Step 5 on a suitable press.
7. Using a suitable air spray system, coat the kernels from Step 6 with a Film-Coat Suspension of Items 6, 7 and 8 in purified water to the desired weight.

What is claimed is:

1. A compound of the formula

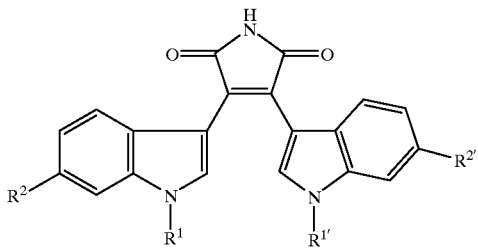

I wherein
$R^1$ and $R^2$ are independently hydrogen or lower alkyl, lower alkenyl or lower alkynyl;
$R^2$ is hydrogen nitro, cyano, halogen, lower alkyl, lower alkenyl, lower alkynyl, or lower alkoxy; and
$R^{2'}$ is a heteroaryl, heterocycle, ethyl substituted with a heteroaryl, or ethoxy substituted with a heteroaryl or heterocycle; or
a pharmaceutically acceptable salt thereof.

2. A compound of claim 1, wherein $R^{2'}$ is a heteroaryl.
3. A compound of claim 2, wherein at least one of $R^1$ and $R^{1'}$ is lower alkyl.
4. A compound of claim 3 wherein at least one of $R^1$ and $R^{1'}$ is methyl.
5. A compound of claim 4, wherein $R^{2'}$ is thiophenyl.
6. A compound of claim 5, wherein the compound is 3-(1-methyl-1H-indol-3-yl)-4-(1-methyl-6-thiophen-2-yl-1H-indol-3-yl)pyrrole-2,5 dione.
7. A compound of claim 5, wherein the compound is 3-(1-methyl-1H-indol-3-yl)-4-(1-methyl-6-thiophen-3-yl-1H-indol-3-yl)pyrrole-2,5-dione.
8. A compound of claim 5, wherein the compound is 3-(1-methyl-6-nitro-1H-indol-3-yl)-4-(1-methyl-6-thiophen-2-yl-1H-indol-3-yl)-pyrrole-2,5-dione.
9. A compound of claim 5, wherein the compound is 3-(1-methyl-6-nitro-1H-indol-3-yl)-4-(1-methyl-6-thiophen-3-yl-1H-indol-3-yl)pyrrole-2,5-dione.
10. A compound of claim 4, wherein $R^{2'}$ is furanyl.
11. A compound of claim 10, wherein the compound is 3-(6-furan-2-yl-1-methyl-1H-indol-3-yl)-4-(1-methyl-1H-indol-3-yl)pyrrole-2,5-dione.
12. A compound of claim 10, wherein the compound is 3-(6-furan-2-yl-1-methyl-1H-indol-3-yl)-4-(1H-indol-3-yl)pyrrole-2,5-dione.
13. A compound of claim 10, wherein the compound is 3-(6-furan-2-yl-1-methyl-1H-indol-3-yl)-4-(1-methyl-6-nitro-1H-indol-3-yl)-pyrrole-2,5-dione.
14. A compound of claim 4, wherein $R^{2'}$ is imidazolyl which is unsubstituted or substituted with lower alkyl.
15. A compound of claim 14, wherein the compound is 3-[1-methyl-6-(1-methyl-1H-imidazol-2-yl)-1H-indol-3-yl]-4-(1-methyl-6-nitro-1H-indol-3-yl)pyrrole-2,5-dione.
16. A compound of claim 14, wherein the compound is 3-(1-methyl-1H-indol-3-yl)-4-[1-methyl-6-(1-methyl-1H-imidazol-2-yl)-1H-indol-3-yl]-pyrrole-2,5-dione.
17. A compound of claim 14, wherein the compound is 3-[1-methyl-6-(3-methyl-3H-imidazol-4-yl)-1H-indol-3-yl]-4-(1-methyl-6-nitro-1H-indol-3-yl)-pyrrole-2,5-dione.
18. A compound of claim 14, wherein the compound is 3-(1-methyl-1H-indol-3-yl)-4-[1-methyl-6-(3-methyl-3H-imidazol-4-yl)-1H-indol-3-yl]pyrrole-2,5-dione.
19. A compound of claim 14, wherein the compound is 3-(6-methoxy-1-methyl-1H-indol-3-yl)-4-[1-methyl-6-(3-methyl-3H-imidazol-4-yl)-1H-indol-3-yl]pyrrole-2,5-dione.
20. A compound of claim 14, wherein the compound is 3-[6-(1-ethyl-1H-imidazol-2-yl)-1H-indol-3-yl]-4-(1-methyl-6-nitro-1H-indol-3-yl)-pyrrole-2,5-dione.
21. A compound of claim 14, wherein the compound is 3-[6-(1H-imidazol-2-yl)-1-methyl-1H-indol-3-yl]-4-(1-methyl-1H-indol-3-yl)-pyrrole-2,5-dione.
22. A compound of claim 14, wherein the compound is 3-[6-(3H-imidazol-4-yl)-1-methyl-1H-indol-3-yl]-4-(1-methyl-6-nitro-1H-indol-3-yl)pyrrole-2,5-dione hydrochloride.
23. A compound of claim 14, wherein the compound is 3-(6-imidazol-1-yl-1-methyl-1H-indol-3-yl)-4-(1-methyl-1H-indol-3-yl)pyrrole-2,5-dione.
24. A compound of claim 14, wherein the compound is 3-(6-imidazol-1-yl-1-methyl-1H-indol-3-yl)-4-(1-methyl-6-nitro-1H-indol-3-yl)-pyrrole-2,5-dione.
25. A compound of claim 14, wherein the compound is 3-(6-imidazol-1-yl-1-methyl-1H-indol-3-yl)-4-(6-methoxy-1-methyl-1H-indol-3-yl)-pyrrole-2,5-dione.

26. A compound of claim 14, wherein the compound is 3-(6-bromo-1-methyl-1H-indol-3-yl)-4-(6-imidazol-1-yl-1-methyl-1H-indol-3-yl)-pyrrole-2,5-dione.

27. A compound of claim 14, wherein the compound is 3-[4-(6-imidazol-1-yl-1-methyl-1H-indol-3-yl)-2,5-dioxo-2,5-dihydro-1H-pyrrol-3-yl]-1-methyl-1H-indole-6-carbonitrile.

28. A compound of claim 14, wherein the compound is 3-[1-methyl-6-(2-methyl-imidazol-1-yl)-1H-indol-3-yl]-4-(1-methyl-6-nitro-1H-indol-3-yl)-pyrrole-2,5-dione.

29. A compound of claim 14, wherein the compound is 3-[6-(1H-imidazol-2-yl)-1-methyl-1H-indol-3-yl]-4-(1-methyl-6-nitro-1H-indol-3-yl)-pyrrole-2,5-dione.

30. A compound of claim 4, wherein $R^2$ is thiazolyl.

31. A compound of claim 30, wherein the compound is 3-(1-methyl-1H-indol-3-yl)-4-(1-methyl-6-thiazol-2-yl-1H-indol-3-yl)-pyrrole-2,5-dione.

32. A compound of claim 30, wherein the compound is 3-(1-methyl-6-nitro-1H-indol-3-yl)-4-(1-methyl-6-thiazol-2-yl-1H-indol-3-yl)pyrrole-2,5-dione.

33. A compound of claim 4, wherein $R^2$ is pyrazolyl, which is unsubstituted or substituted with lower alkyl.

34. A compound of claim 33, wherein the compound is 3-(1-methyl-6-nitro-1H-indol-3-yl)-4-(1-methyl-6-pyrazol-1-yl-1H-indol-3-yl)pyrrole-2,5-dione.

35. A compound of claim 33, wherein the compound is 3-(1-methyl-1H-indol-3-yl)-4-(1-methyl-6-pyrazol-1-yl-1H-indol-3-yl)pyrrole-2,5-dione.

36. A compound of claim 33, wherein the compound is 3-(6-bromo-1-methyl-1H-indol-3-yl)-4-(1-methyl-6-pyrazol-1-yl-1H-indol-3-yl)pyrrole-2,5-dione.

37. A compound of claim 33, wherein the compound is 3-[1-methyl-6-(2-methyl-2H-pyrazol-3-yl)-1H-indol-3-yl]-4-(1-methyl-6-nitro-1H-indol-3-yl)pyrrole-2,5dione.

38. A compound of claim 33, wherein the compound is 3-(1-methyl-1H-indol-3-yl)-4-[1-methyl-6-(2-methyl-2H-pyrazol-3-yl)-1H-indol-3-yl]pyrrole-2,5-dione.

39. A compound of claim 33, wherein the compound is 3-(6-bromo-1-methyl-1H-indol-3-yl)-4-[1-methyl-6-(2-methyl-2H-pyrazol-3-yl)-1H-indol-3-yl]pyrrole-2,5-dione.

40. A compound of claim 4, wherein $R^{2'}$ is a pyrimidinyl.

41. A compound of claim 40, wherein the compound is 3-(1-methyl-6-nitro-1H-indol-3-yl)-4-(1-methyl-6-pynimidin-5-yl-1H-indol-3-yl)pyrrole-2,5-dione.

42. A compound of claim 40, wherein the compound is 3-(1-methyl-1H-indol-3-yl)-4-(1-methyl-6-pyrimidin-5-yl-1H-indol-3-yl)pyrrole-2,5-dione.

43. A compound of claim 4, wherein R2' is an isothiazolyl.

44. A compound of claim 43, wherein the compound is 3-(6-isothiazol-5-yl-1-methyl-1H-indol-3-yl)-4-(1-methyl-6-nitro-1H-indol-3-yl)pyrrole-2,5-dione.

45. A compound of claim 43, wherein the compound is 3-(6-isothiazol-5-yl-1-methyl-1H-indol-3-yl)-4-(1-methyl-1H-indol-3-yl)-pyrrole-2,5-dione.

46. A compound of claim 1, wherein $R^{2'}$ is a heterocycle.

47. A compound of claim 46, wherein at least one of $R^1$ and $R^{1'}$ is lower alkyl.

48. A compound of claim 47, wherein at least one of $R^1$ and $R^{1'}$ is methyl.

49. A compound of claim 48, wherein $R^{2'}$ is piperazine which is unsubstituted or substituted with lower alkyl, lower alkoxy or carbonyl.

50. A compound of claim 49, wherein $R^{2'}$ is piperazine which is substituted with lower alkyl.

51. A compound of claim 50, wherein R2' is 4-methyl-piperazinyl.

52. A compound of claim 51, wherein the compound is 3-(1-methyl-1H-indol-3-yl)-4-[1-methyl-6-(4-methyl-piperazin-1-yl)-1H-indol-3-yl]pyrrole-2,5-dione.

53. A compound of claim 48, wherein $R^{2'}$ is pyrrolidinyl.

54. A compound of claim 53, wherein the compound is 3-(1-methyl-6-nitro-1H-indol-3-yl)-4-(1-methyl-6-pyrrolidin-1-yl-1H-indol-3-yl)pyrrole-2,5-dione.

55. A compound of claim 53, wherein the compound is 3-(1-methyl-6-nitro-1H-indol-3-yl)-4-(6-pyrrolidin-1-yl-1H-indol-3-yl)pyrrole-2,5-dione.

56. A compound of claim 53, wherein the compound is 3-(6-fluoro-1-methyl-1H-indol-3-yl)-4-(6-pyrrolidin-1-yl-1H-indol-3-yl)pyrrole-2,5-dione.

57. A compound of claim 53, wherein the compound is 3-(6-chloro-1-methyl-1H-indol-3-yl)-4-(6-pyrrolidin-1-yl-1H-indol-3-yl)pyrrole-2,5-dione.

58. A compound of claim 53, wherein the compound is 3-(1-methoxymethyl-6-pyrrolidin-1-yl-1H-indol-3-yl)-4-(1-methyl-6-nitro-1H-indol-3-yl)pyrrole-2,5-dione.

59. A compound of claim 53, wherein the compound is 3-(6-bromo-1-methyl-1H-indol-3-yl)-4-(1-methyl-6-pyrrolidin-1-yl-1H-indol-3-yl)pyrrole-2,5-dione.

60. A compound of claim 53, wherein the compound is 3-(6-methoxy-1-methyl-1 1H-indol-3-yl)-4-(1-methyl-6-pyrrolidin-1-yl-1H-indol-3-yl)pyrrole-2,5-dione.

61. A compound of claim 53, wherein the compound is 3-(1-methyl-6-pyrrolidin-1-yl-1H-indol-3-yl)-4-(1-methyl-6-trifluoromethyl-1H-indol-3-yl)pyrrole-2,5-dione.

62. A compound of claim 53 wherein the compound is 3-(1-methyl-1H-indol-3-yl)-4-(1-methyl-6-pyrrolidin-1-yl-1H-indol-3-yl)pyrrole-2,5-dione.

63. A compound of claim 53, wherein the compound is 1-methyl-3-[4-(1-methyl-6-pyrrolidin-1-yl-1H-indol-3-yl)-2,5-dioxo-2,5-dihydro-1H-pyrrol-3-yl]-1H-6-carbonitrile.

64. A compound of claim 53, wherein the compound is 3-(1H-indol-3-yl)-4-(1-methyl-6-pyrrolidin-1-yl-1H-indol-3-yl)-pyrrole-2,5-dione.

65. A compound of claim 53, wherein the compound is 3-(6-chloro-1-methyl-1H-indol-3-yl)-4-(1-methyl-6-pyrrolidin-1-yl-1H-indol-3-yl)pyrrole-2,5-dione.

66. A compound of claim 48, wherein $R^{2'}$ is piperidinyl.

67. A compound of claim 66, wherein the compound is 3-(1-methyl-1H-indol-3-yl)-4-(1-methyl-6-piperidin-1-yl-1H-indol-3-yl)pyrrole-2,5-dione.

68. A compound of claim 48, wherein $R^{2'}$ is morpholinyl.

69. A compound of claim 68, wherein the compound is 3-(1-methyl-6-morpholin-4-yl-1H-indol-3-yl)-4-(1-methyl-6-nitro-1H-indol-3-yl)pyrrole-2,5-dione.

70. A compound of claim 68, wherein the compound is 3-(1-methyl-1H-indol-3-yl)-4-(1-methyl-6-morpholin-4-yl-1H-indol-3-yl)pyrrole-2,5-dione.

71. A compound of claim 68, wherein the compound is 1-methyl-3-[4-(1-methyl-6-morpholin-4-yl-1H-indol-3-yl)-2,5-dioxo-2,5-dihydro-1H-pyrrol-3-yl]-1H-indole-6-carbonitrile.

72. A compound of claim 68, wherein the compound is 3-(6-methoxy-1-methyl-1H-indol-3-yl)-4-(1-methyl-6-morpholin-4-yl-1H-indol-3-yl)pyrrole-2,5-dione.

73. A compound of claim 68, wherein the compound is 3-(6-fluoro-1-methyl-1H-indol-3-yl)-4-(1-methyl-6-morpholin-4-yl-1H-indol-3-yl)pyrrole-2,5-dione.

74. A compound of claim 68, wherein the compound is 3-(6-chloro-1-methyl-1H-indol-3-yl)-4-(1-methyl-6-morpholin-4-yl-1H-indol-3-yl)pyrrole-2,5-dione.

75. A compound of claim 68, wherein the compound is 3-(6-bromo-1-methyl-1H-indol-3-yl)-4-(1-methyl-6-morpholin-4-yl-1H-indol-3-yl)pyrrole-2,5-dione.

76. A compound of claim 68, wherein the compound is 3-(1-methyl-6-morpholin-4-yl-1H-indol-3-yl)-4-(1-methyl-6-trifluoromethyl-1H-indol-3-yl)pyrrole-2,5-dione.

77. A compound of claim 68, wherein the compound is 3-(1,6-dimethyl-1H-indol-3-yl)-4-(1-methyl-6-morpholin-4-yl-1H-indol-3-yl)pyrrole-2,5-dione.

78. A compound of claim 68, wherein the compound is 3-(1H-indol-3-yl)-4-(1-methyl-6-morpholin-4-yl-1H-indol-3-yl)pyrrole-2,5-dione.

79. A compound of claim 68, wherein the compound is 3-(6-fluoro-1-methyl-1H-indol-3-yl)-4-(1-methoxymethyl-6-morpholin-4-yl-1H-indol-3-yl)pyrrole-2,5-dione.

80. A compound of claim 68, wherein the compound is 3-(6-fluoro-1-methyl-1H-indol-3-yl)-4-(6-morpholin-4-yl-1H-indol-3-yl)-pyrrole-2,5-dione.

81. A compound of claim 68, wherein the compound is 3-(1-methyl-1H-indol-3-yl)-4-(6-morpholin-4-yl-1H-indol-3-yl)pyrrole-2,5-dione.

82. A compound of claim 1, wherein $R^{2'}$ is an ethoxy substituted by a heteroaryl or heterocycle.

83. A compound of claim 82, wherein at least one of $R^1$ and $R^{1'}$ is lower alkyl.

84. A compound of claim 82, wherein at least one of $R^1$ and $R^{1'}$ is methyl.

85. A compound of claim 84, wherein $R^{2'}$ is ethoxy substituted by a heteroaryl.

86. A compound of claim 85, wherein the heteroaryl is imidazolyl.

87. A compound of claim 86, wherein the compound is 3-[6-(2-imidazol-1-yl-ethoxy)-1-methyl-1H-indol-3-yl]-4-(1-methyl-6-nitro-1H-indol-3-yl)pyrrole-2,5-dione.

\* \* \* \* \*

UNITED STATES PATENT AND TRADEMARK OFFICE
CERTIFICATE OF CORRECTION

PATENT NO. : 6,281,356 B1
DATED : August 28, 2001
INVENTOR(S) : Fotouhi et al.

It is certified that error appears in the above-identified patent and that said Letters Patent is hereby corrected as shown below:

Column 38, claim 60,
Line 21, delete "3-(6-methoxy-1-methyl-1 1H-indol-3-yl)-4-(1-methyl-6-" and replace with -- 3-(6-methoxy-1-methyl-1H-indol-3-yl)-4-(1-methyl-6- --.

Signed and Sealed this

Twenty-sixth Day of February, 2002

Attest:

JAMES E. ROGAN
Attesting Officer    Director of the United States Patent and Trademark Office